United States Patent
Estes et al.

(10) Patent No.: US 7,828,528 B2
(45) Date of Patent: Nov. 9, 2010

(54) OCCLUSION SENSING SYSTEM FOR INFUSION PUMPS

(75) Inventors: Mark C. Estes, Simi Valley, CA (US); Mitchell Wenger, Ross, CA (US); John W. Sadler, Belmont, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 523 days.

(21) Appl. No.: 11/851,212

(22) Filed: Sep. 6, 2007

(65) Prior Publication Data

US 2009/0067989 A1 Mar. 12, 2009

(51) Int. Cl.
*F04B 49/10* (2006.01)
*A61M 35/00* (2006.01)

(52) U.S. Cl. .............................. 417/43; 417/53; 604/67; 604/890.1

(58) Field of Classification Search .................. 417/43, 417/53, 300; 604/67, 890.1
See application file for complete search history.

(56) References Cited

U.S. PATENT DOCUMENTS

| | | | |
|---|---|---|---|
| 2,605,765 | A | 8/1952 | Kollsman |
| 3,886,938 | A | 6/1975 | Szabo et al. |
| 4,077,405 | A | 3/1978 | Haerten et al. |
| 4,231,368 | A | 11/1980 | Becker |
| 4,265,241 | A | 5/1981 | Portner et al. |
| 4,300,554 | A | 11/1981 | Hessberg et al. |
| 4,313,439 | A | 2/1982 | Babb et al. |
| 4,398,908 | A | 8/1983 | Siposs |
| 4,435,173 | A | 3/1984 | Siposs et al. |
| 4,443,218 | A | 4/1984 | DeCant, Jr. et al. |
| 4,493,704 | A | 1/1985 | Beard et al. |
| 4,529,401 | A | 7/1985 | Leslie et al. |
| 4,627,835 | A | * 12/1986 | Fenton, Jr. .................... 604/67 |
| 4,850,817 | A | 7/1989 | Nason et al. |
| 5,045,064 | A | 9/1991 | Idriss |
| 5,088,981 | A | 2/1992 | Howson et al. |
| 5,190,522 | A | 3/1993 | Wojcicki et al. |
| 5,250,027 | A | 10/1993 | Lewis et al. |
| 5,261,882 | A | 11/1993 | Sealfon et al. |
| 5,314,412 | A | 5/1994 | Rex |
| 5,335,994 | A | 8/1994 | Weynant Nee Girones |

(Continued)

FOREIGN PATENT DOCUMENTS

CA 2543545 5/2005

(Continued)

OTHER PUBLICATIONS

U.S. Appl. No. 11/362,616.

(Continued)

*Primary Examiner*—Devon C Kramer
*Assistant Examiner*—Bryan Lettman
(74) *Attorney, Agent, or Firm*—Fish & Richardson P.C.

(57) ABSTRACT

Some embodiments of an infusion pump system may include an occlusion sensor system that communicates with control circuitry to detect the presence of an occlusion. In some embodiments, the occlusion sensor system includes first components that are located within a disposable and non-reusable pump device, and second components that are located within a reusable controller device, the second components being in operable communication with the first components to determine whether a fluid is flowing from the pump device.

30 Claims, 21 Drawing Sheets

U.S. PATENT DOCUMENTS

| | | | |
|---|---|---|---|
| 5,338,157 A | 8/1994 | Blomquist | |
| 5,342,180 A | 8/1994 | Daoud | |
| 5,395,340 A | 3/1995 | Lee | |
| 5,411,487 A | 5/1995 | Castagna | |
| 5,445,622 A | 8/1995 | Brown | |
| 5,462,525 A | 10/1995 | Srisapthapat et al. | |
| 5,545,143 A | 8/1996 | Fischell et al. | |
| 5,551,850 A | 9/1996 | Williamson et al. | |
| 5,569,186 A | 10/1996 | Lord et al. | |
| 5,626,566 A | 5/1997 | Petersen et al. | |
| 5,637,095 A | 6/1997 | Nason et al. | |
| 5,665,065 A | 9/1997 | Colman et al. | |
| 5,727,933 A * | 3/1998 | Laskaris et al. | 418/2 |
| 5,741,216 A | 4/1998 | Hemmingsen et al. | |
| 5,772,635 A | 6/1998 | Dastur et al. | |
| 5,816,306 A | 10/1998 | Giacomel | |
| 5,852,803 A | 12/1998 | Ashby, III et al. | |
| 5,919,167 A | 7/1999 | Mulhauser et al. | |
| 5,925,018 A | 7/1999 | Ungerstedt | |
| 5,928,201 A | 7/1999 | Poulsen et al. | |
| 5,947,934 A | 9/1999 | Hansen et al. | |
| 5,951,530 A | 9/1999 | Steengaard et al. | |
| 5,957,889 A | 9/1999 | Poulsen et al. | |
| 5,984,894 A | 11/1999 | Poulsen et al. | |
| 5,984,897 A | 11/1999 | Petersen et al. | |
| 5,997,475 A | 12/1999 | Bortz | |
| 6,003,736 A | 12/1999 | Ljunggren | |
| 6,010,485 A | 1/2000 | Buch-Rasmussen et al. | |
| 6,033,377 A | 3/2000 | Rasmussen et al. | |
| 6,045,537 A | 4/2000 | Klitmose | |
| 6,074,372 A | 6/2000 | Hansen | |
| 6,110,149 A | 8/2000 | Klitgaard et al. | |
| 6,156,014 A | 12/2000 | Petersen et al. | |
| 6,171,276 B1 | 1/2001 | Lippe et al. | |
| 6,231,540 B1 | 5/2001 | Smedegaard | |
| 6,248,067 B1 | 6/2001 | Causey, III et al. | |
| 6,248,090 B1 | 6/2001 | Jensen et al. | |
| 6,248,093 B1 | 6/2001 | Moberg | |
| 6,277,098 B1 | 8/2001 | Klitmose et al. | |
| 6,302,855 B1 | 10/2001 | Lav et al. | |
| 6,302,869 B1 | 10/2001 | Klitgaard | |
| 6,375,638 B2 | 4/2002 | Nason et al. | |
| 6,379,339 B1 | 4/2002 | Klitgaard et al. | |
| 6,381,496 B1 | 4/2002 | Meadows et al. | |
| 6,404,098 B1 | 6/2002 | Kayama et al. | |
| 6,427,088 B1 | 7/2002 | Bowman, IV et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,589,229 B1 * | 7/2003 | Connelly et al. | 604/890.1 |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 | 12/2003 | Mahoney et al. | |
| 6,656,159 B2 | 12/2003 | Flaherty | |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,690,192 B1 | 2/2004 | Wing | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,198 B2 | 4/2004 | Larsen | |
| 6,723,072 B2 | 4/2004 | Flaherty et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |
| 6,768,425 B2 | 7/2004 | Flaherty et al. | |
| 6,780,156 B2 | 8/2004 | Haueter et al. | |
| 6,786,246 B2 | 9/2004 | Ohms et al. | |
| 6,786,890 B2 | 9/2004 | Preuthun et al. | |
| 6,796,970 B1 | 9/2004 | Klitmose et al. | |
| 6,799,149 B2 | 9/2004 | Hartlaub | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,827,702 B2 | 12/2004 | Lebel et al. | |
| 6,830,558 B2 | 12/2004 | Flaherty et al. | |
| 6,852,104 B2 | 2/2005 | Blomquist | |
| 6,854,620 B2 | 2/2005 | Ramey | |
| 6,854,653 B2 | 2/2005 | Eilersen | |
| 6,855,129 B2 | 2/2005 | Jensen et al. | |
| 6,872,200 B2 | 3/2005 | Mann et al. | |
| 6,873,268 B2 | 3/2005 | Lebel et al. | |
| 6,878,132 B2 | 4/2005 | Kipfer | |
| 6,893,415 B2 | 5/2005 | Madsen et al. | |
| 6,899,695 B2 | 5/2005 | Herrera | |
| 6,899,699 B2 | 5/2005 | Enggaard | |
| 6,922,590 B1 | 7/2005 | Whitehurst | |
| 6,936,006 B2 | 8/2005 | Sabra | |
| 6,936,029 B2 | 8/2005 | Mann et al. | |
| 6,945,961 B2 | 9/2005 | Miller et al. | |
| 6,948,918 B2 | 9/2005 | Hansen | |
| 6,950,708 B2 | 9/2005 | Bowman, IV et al. | |
| 6,960,192 B1 | 11/2005 | Flaherty et al. | |
| 6,979,326 B2 | 12/2005 | Mann et al. | |
| 6,997,911 B2 | 2/2006 | Klitmose | |
| 6,997,920 B2 | 2/2006 | Mann et al. | |
| 7,005,078 B2 | 2/2006 | Van Lintel et al. | |
| 7,008,399 B2 | 3/2006 | Larson et al. | |
| 7,014,625 B2 | 3/2006 | Bengtsson | |
| 7,018,360 B2 | 3/2006 | Flaherty et al. | |
| 7,025,743 B2 | 4/2006 | Mann | |
| 7,029,455 B2 | 4/2006 | Flaherty | |
| 7,054,836 B2 | 5/2006 | Christensen et al. | |

| | | |
|---|---|---|
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0128594 A1* | 9/2002 | Das et al. ............... 604/67 |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0167035 A1 | 9/2003 | Flaherty et al. |
| 2003/0199825 A1 | 10/2003 | Flaherty |
| 2003/0216683 A1 | 11/2003 | Shekalim |
| 2003/0233069 A1* | 12/2003 | Gillespie et al. ........ 604/131 |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |

FOREIGN PATENT DOCUMENTS

| | | |
|---|---|---|
| DE | 196 27 619 A | 1/1998 |
| DE | 102 36 669 A | 2/2004 |
| DE | 103 39 906 | 3/2005 |
| DE | 10339906 | 10/2009 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |
| WO | WO 2006/110913 | 10/2006 |

OTHER PUBLICATIONS

Medtronic News Release, "Medtronic Receives FDA Approval for World's First Insulin Pump with Real-time Continuous Glucose Monitoring," Apr. 13, 2006, 3 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Patent Abstracts of Japan, vol. 1999, No. 4, and JP 11 010036, Apr. 30, 1999 and Jan. 19, 1999, Toray Ind. Inc.

International Search Report & Written Opinion, PCT/US2008/069619, mailed Oct. 22, 2008, 17 pages.

European Patent Office, International Preliminary Report on Patentability for Application No. PCT/US2008/069619, dated Mar. 18, 2010, 9 pages.

* cited by examiner

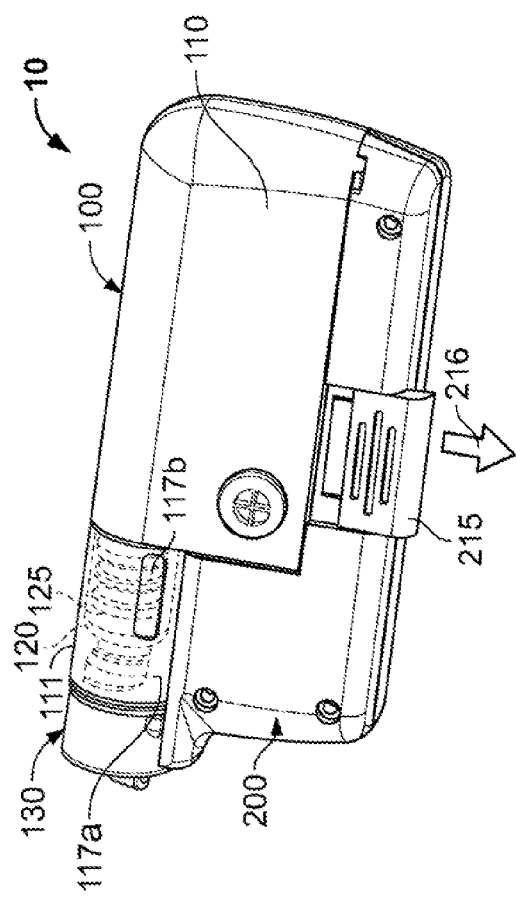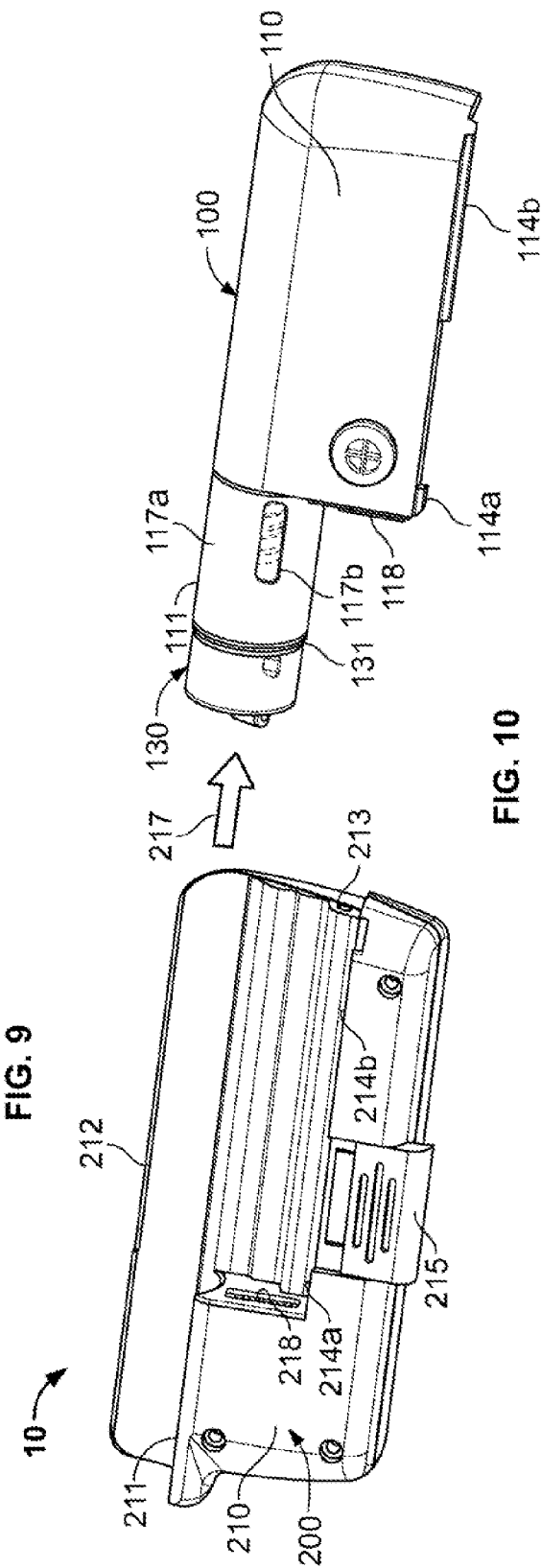

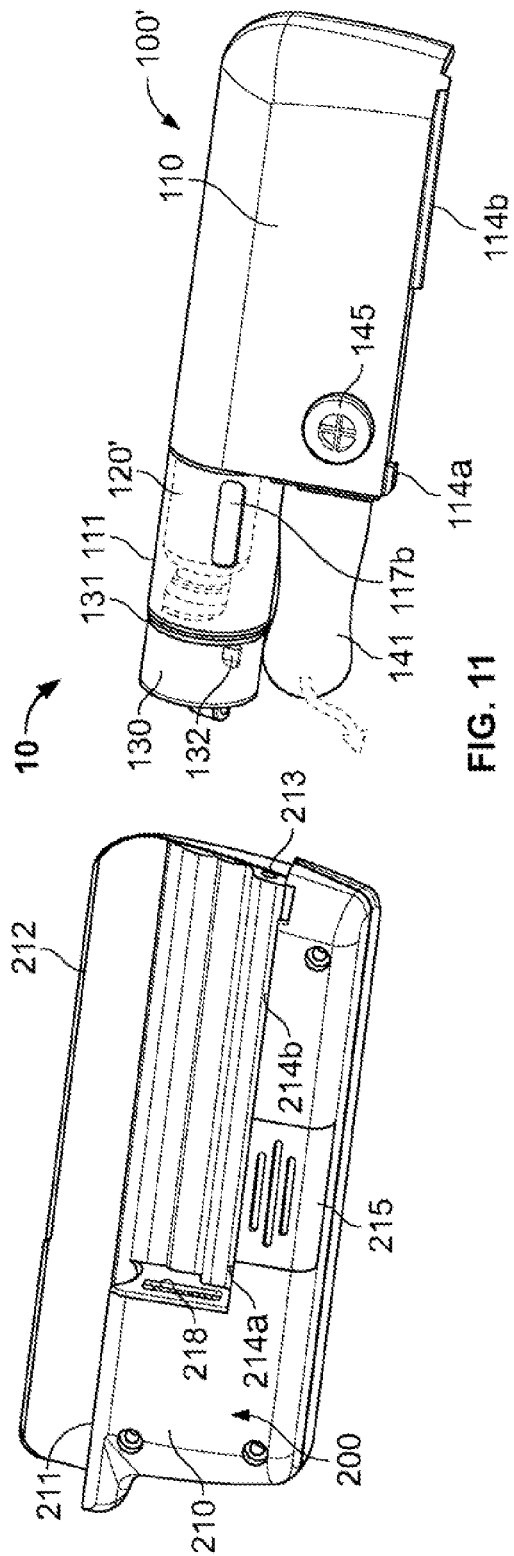
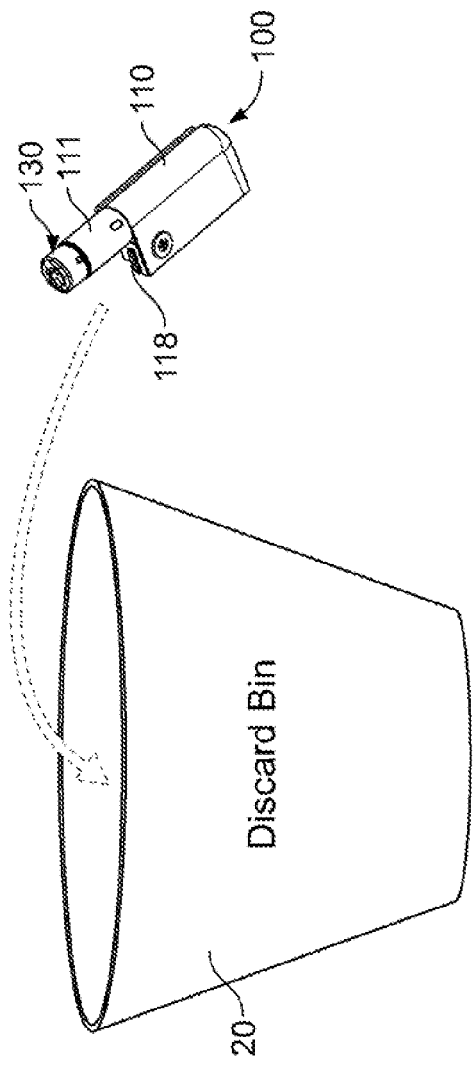
FIG. 11
FIG. 12

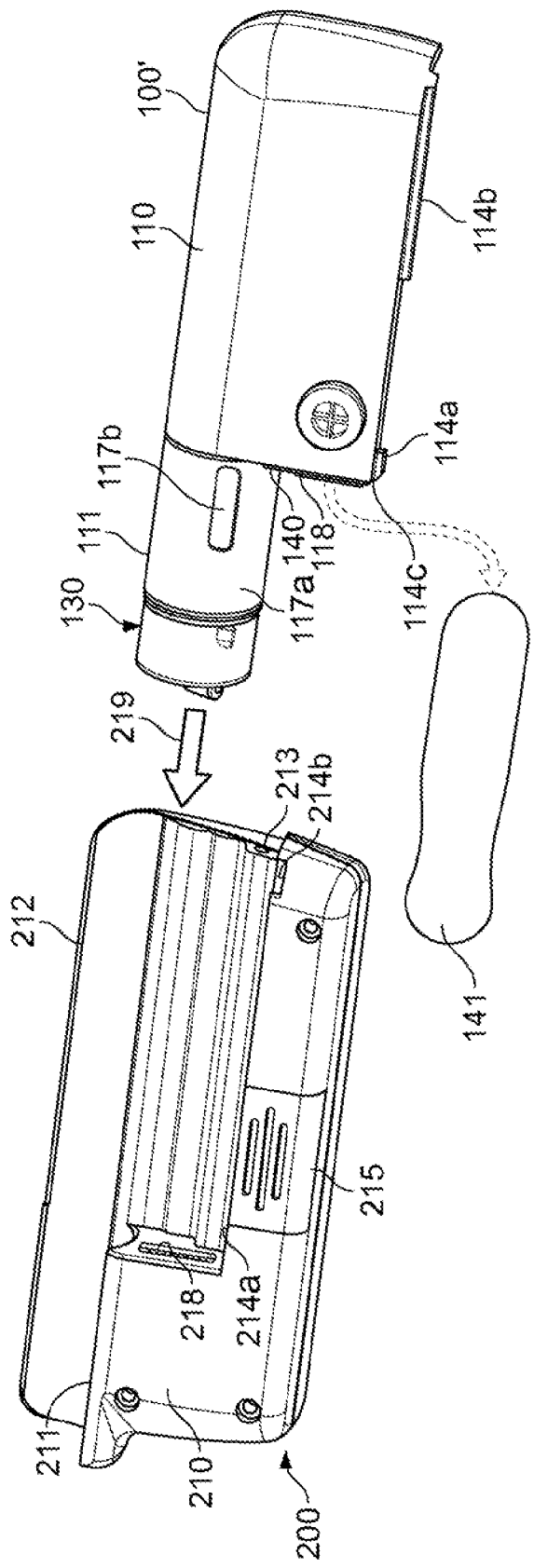
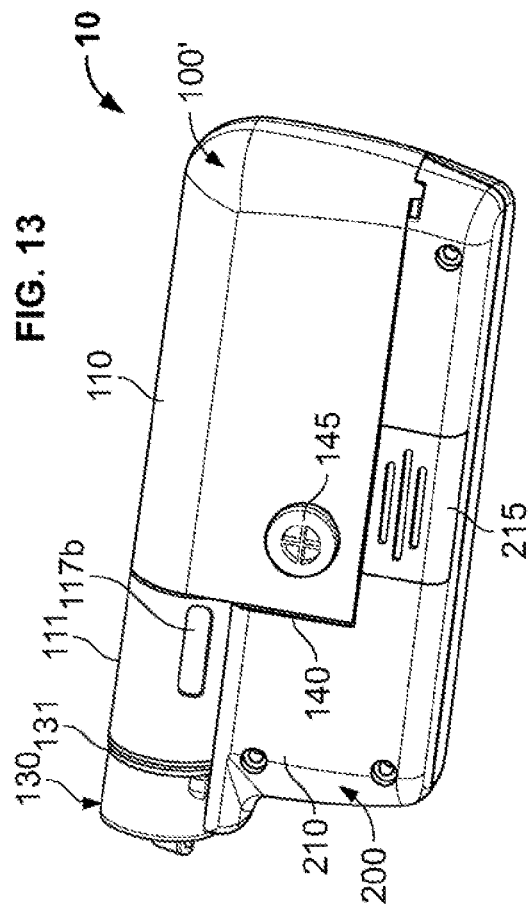
FIG. 13
FIG. 14

OCCLUSION SENSING SYSTEM FOR INFUSION PUMPS

TECHNICAL FIELD

This document relates to configurations of an infusion pump system, such as a wearable infusion pump system for the delivery of medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

SUMMARY

Some embodiments of an infusion pump system can include an occlusion sensor system having a flow-responsive member that moves in response to a medicine flow through a flow chamber. A sensor circuit can monitor movement of the flow-responsive member and can generate a signal indicative of the presence or absence of the medicine flow based on movement or non-movement of the flow responsive member. In other embodiments, an occlusion sensor system includes an obstruction member that generates disturbances in a medicine flow path when medicine flows through a flow chamber. A sensor circuit can monitor the disturbances and can generate a signal indicative of the presence or absence of the medicine flow, based on the presences or absence of the disturbances.

Some or all of the embodiments of the occlusion sensor system described herein may provide one or more of the following advantages. First, some components of the occlusion sensor system can be low-cost components, which are readily manufactured with the pump device without adding significant expense. Part of the occlusion sensor system can be arranged in a disposable and non-reusable pump device of the infusion pump system. As such, disposal of the pump device is not cost-prohibitive, because other, potentially more costly components of the occlusion sensor system can be located in the reusable controller device. In this manner, a simple, cost-effective solution can be provided for occlusion detection. Further, the occlusion detection can occur immediately upon activation of the pump device. In this manner, a user can be more rapidly alerted as to the presence of an occlusion. This is particularly advantageous when compared to other occlusion detectors, which may require an extended monitoring period before alerting a user.

Some embodiments of a wearable infusion pump system include a disposable and non-reusable pump device including a drive system to dispense medicine from the pump device, the pump device having a first electrical connector that is externally accessible, and a reusable controller device removably attachable to the disposable and non-reusable pump device. The controller device can include a second electrical connector that is engageable with the first connector to provide electrical communication between control circuitry of the controller device and the drive system of the pump device. An occlusion sensor system can communicate with the control circuitry to detect the presence of an occlusion in a medicine flow path. Embodiments of the occlusion sensor system include a flow-responsive component arranged within a flow chamber of the pump device, the flow-responsive component moving in the flow chamber in response to medicine flow through the flow chamber and acting on the flow-responsive component. A sensor circuit can be at least partially disposed within the controller device, the sensor circuit being arranged to detect movement of the flow-responsive component to a first position. The sensor circuit can communicate a signal to the control circuitry in response to the movement of the flow-responsive component to the first position.

Particular embodiments of a method of monitoring a wearable infusion pump system for occlusions include preparing a pump device for use with a controller device, the pump device including at least a portion of a drive system to dispense medicine from the pump device, the controller device including control circuitry to communicate control signals to the drive system of the pump device. The pump device can be removably attached with the controller device so that a first electrical connector of the pump device engages a second electrical connector of the controller device. A flow-responsive component of an occlusion sensor system can be aligned with a sensor circuit of the occlusion sensor system, the flow-responsive component being movable within a flow chamber of the pump device and the sensor circuit being at least partially disposed within the controller device. The occlusion sensor system can be activated to determine if the medicine is flowing from the pump device.

Further embodiments of a portable and wearable infusion pump assembly can include a disposable and non-reusable pump device including: a drive system to dispense a medicine from the pump device, a pump housing to enclose at least a portion of the drive system, and a first electrical connector that is externally accessible along the pump housing, and a reusable controller device removably attached to the pump device. The controller device can include: a user interface having a display device and at least one button, control circuitry to communicate with the drive system of the pump device, a controller housing to enclose at least a portion of the control circuitry, and a second electrical connector is engaged with the first connector to provide electrical communication between the control circuitry and the drive system. An occlusion sensor system that communicates with the control circuitry to detect the presence of an occlusion in a medicine flow path can be provided. The occlusion sensor system can include a flow-responsive component arranged within a flow chamber of the pump device, the flow-responsive component moving in the flow chamber in response to medicine flow through the flow chamber and acting on the flow-responsive component. A sensor circuit can be at least partially disposed within the controller device, the sensor circuit being arranged to detect movement of the flow-responsive component to a first position, the sensor circuit communicating a signal to the control circuitry in response to the movement of the flow-responsive component to the first position.

Other embodiments of a wearable infusion pump system can include a disposable and non-reusable pump device including a drive system to dispense medicine from the pump device, the pump device having a first electrical connector that is externally accessible, and a reusable controller device removably attachable to the disposable and non-reusable pump device, the controller device including a second electrical connector that is engageable with the first connector to provide electrical communication between control circuitry of the controller device and the drive system of the pump device. An occlusion sensor system can be provided that communicates with the control circuitry to detect the presence of an occlusion in a medicine flow path. The occlusion sensor system can include an obstruction member arranged within a flow chamber of the pump device, the obstruction member arranged in a medicine flow path to generate disturbances within the medicine flow path, and a sensor circuit at least partially disposed within the controller device. The sensor circuit can be arranged to detect the disturbances in the medicine flow path and communicate a signal to the control circuitry in response to the disturbances.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 9-10 are perspective views of a pump device being detached from a controller device, in accordance with some embodiments.

FIGS. 11-12 are perspective views of the pump device of FIGS. 9-10 being discarded and the controller device of FIGS. 9-10 being reused with a new pump device.

FIGS. 13-14 are perspective views of the new pump device of FIG. 11 being attached to the controller device of FIG. 11.

Like reference symbols in the various drawings indicate like elements.

DETAILED DESCRIPTION OF ILLUSTRATIVE EMBODIMENTS

Figure 1:
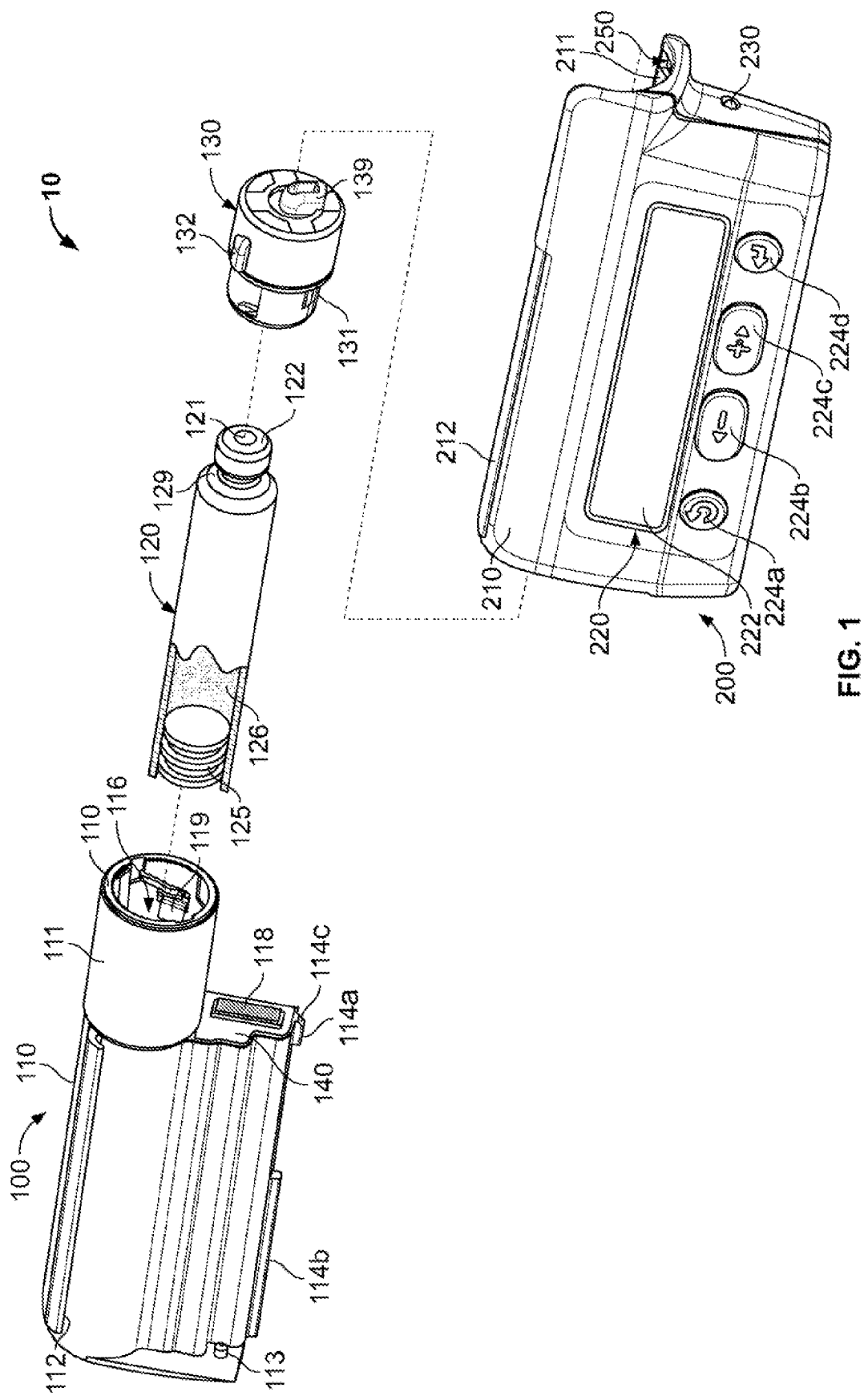
FIG. 1 is a perspective view of an infusion pump system in accordance with some embodiments, in accordance with some embodiments.
Figure 2:
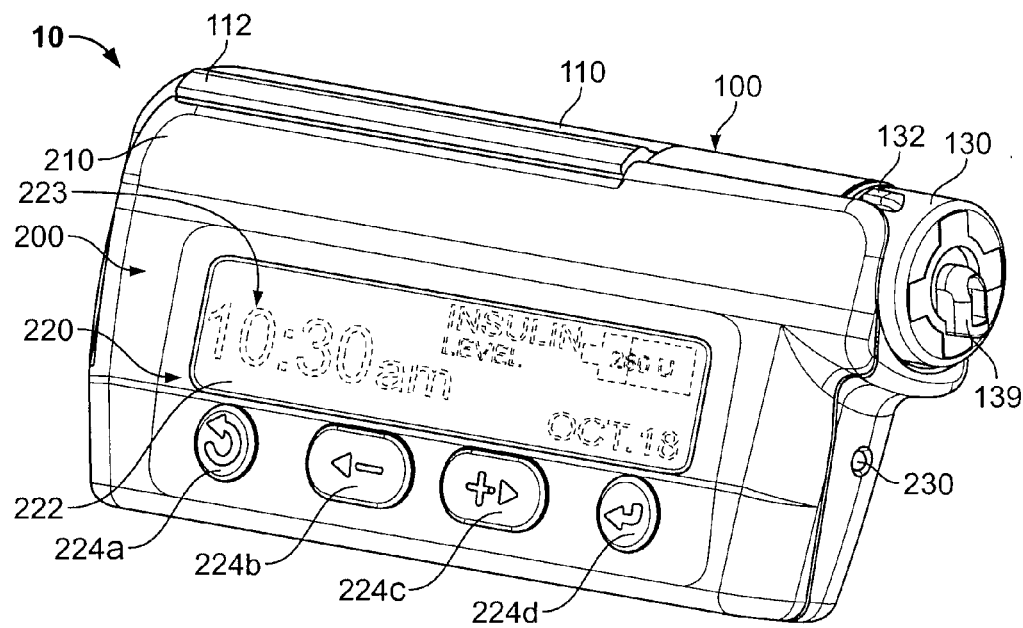
FIG. 2 is a perspective view of the infusion pump system of FIG. 1 in an assembled state.
Figure 3:
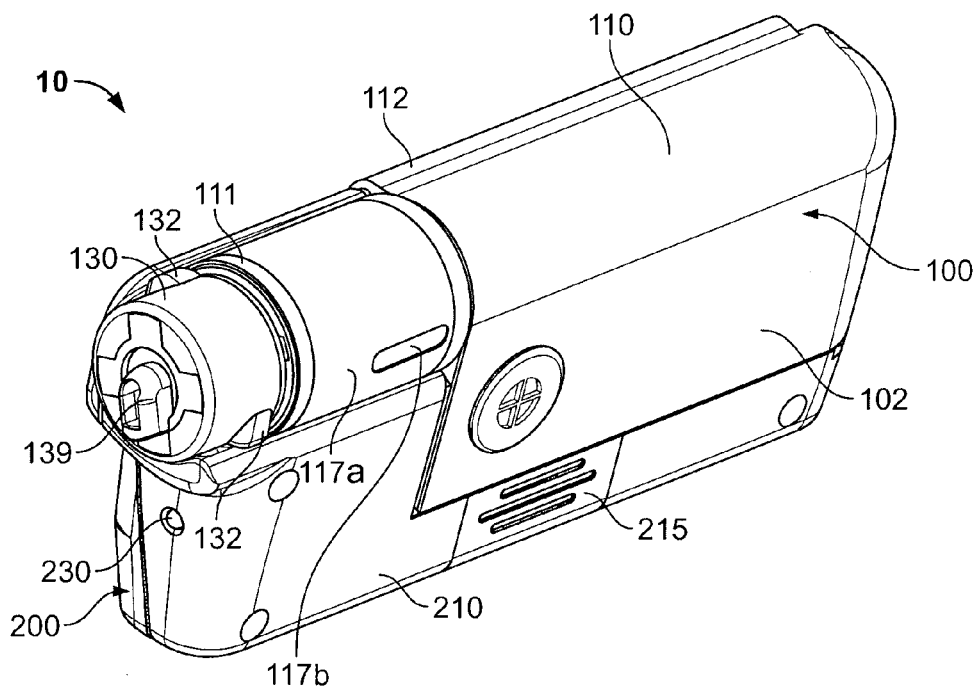
FIG. 3 is another perspective view of the infusion pump system of FIG. 2.

Referring to FIGS. 1-3, an infusion pump system 10 can include a pump device 100 and a controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

The infusion pump system 10 also includes an occlusion sensor system 250 for prompt detection of an occlusion in the medicine flow path. This sensor system 250 may be a flow-based detection system. For example, the occlusion sensor system may include one or more flow-responsive instruments that physically move in a flow chamber in response to medicine flow through the flow chamber. As described in more detail below in connection with FIGS. 19-31, the occlusion sensor system 250 can include some components that are housed within the pump device 100 and other components that are housed within the controller device 200. The sensor components housed by the pump device 100 operably communicate with that are those housed by the controller device 200 upon attachment of the pump device 100 to the controller device 200. Further, the sensor components arranged in the pump device 100 can be relatively low-cost components that are readily manufactured with the pump device 100. In this manner, a simple, cost-effective solution is provided for occlusion detection in the infusion pump system 10. Further, the occlusion detection can occur immediately upon activation of the pump device 100 to deliver medicine. As described in further detail below, the sensor components of the various embodiments of the occlusion sensor system 250 are immediately responsive to fluid flow. Consequently, movement, rotation and/or oscillation of the sensor components can be instantaneously detected upon activation of the pump device 100.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 includes a housing 210 having a number of features that mate with complementary features of the pump housing 110. In such circumstances, the controller device 200 can removably attach with the pump device 100 in a generally side-by-side configuration while not fully surrounding the pump housing 110. Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable (as described below in connection with FIGS. 6-8). Moreover, at least one of the pump device 100 or the controller device 200 may include a release member that facilitates an easy-to-use detachment and replacement process. For example, as described in more detail below in connection with FIGS. 9-14, an exhausted pump device 100 may be a "one time use" component that is discarded after being used, and a new pump device 100' (having a new medicine cartridge 120') can thereafter be attached to the controller device 200.

Furthermore, in use, the controller device 200 can include a sensor configuration that detects occlusions in the fluid flow path extending to the user. For example, the controller device 200 may include the occlusion sensor system 250 that detects the fluid flow through the cap device 130. As described in more detail below in connection with FIGS. 19-31, the occlusion sensor system 250 may include optical sensor components, acoustical sensor components, electromagnetic sensor components, or a combination thereof.

Referring again to FIGS. 1-3, in this embodiment, the pump system 10 is a medical infusion pump system that is configured to controllably dispense a medicine from the cartridge 120. As such, the fluid cartridge 120 may contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 1, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 1) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100.

Such a configuration may facilitate the "one-time-use" feature of the pump device 100. Because the retainer wings 119 interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the cap device 130 can be joined with the pump device 100 after the medicine cartridge is inserted in the cavity 116. In this embodiment, the cap device 130 is multifunctional in that it performs a number of functions for the pump device operation. For example, attachment of the cap device 130 may cause one or more of the following preparatory functions: forcing the plunger 125 (FIG. 1) of the fluid cartridge 120 to engage with the piston rod (not shown in FIGS. 1-3, refer for example to FIG. 17), piercing a septum 121 of the fluid cartridge 120 to provide a flow path for the fluid (refer for example to FIG. 20), and priming the fluid cartridge 120 with a "break away" force to initiate movement of the plunger 125 in the fluid cartridge 120. In addition or in the alternative, attachment of the cap device 130 may also cause one or more of the following safety related functions: aligning the occlusion sensor system 250 with the a portion of the fluid flow path (described in connection with FIGS. 19-31), sealing the pump housing 110 (e.g., using a polymeric o-ring seal 131 or the like) to resist migration of external contaminants into the cavity 116, and ceasing or preventing the dispensation of fluid if the cap device 130 is improperly engaged with the pump housing 110. In other embodiments, the cap device 130 may supplement or replace the previously described retainer wings 119 by locking into position after joining with the pump housing 110, thereby hindering removal of the fluid cartridge 120 in the pump housing 110.

The cap device 130 can include one or more alignment tabs 132 that operate to ensure that the cap device 130 is joined with the pump housing 110 in a selected orientation. For example, as shown in FIGS. 2-3, the cap device 130 may include an output port 139 that connects with tubing (e.g., FIG. 6) for dispensation of the medicine to the user. The output port 139 may have an angled orientation such that a portion of the tubing extends transversely to the central axis of the cartridge 120 and cap device 130. The alignment tabs 132 arranged on the body of the cap device 130 can align with adjacent surfaces of the controller housing 210 to provide the selected orientation of the output port during operation. If, for example, the cap device 130 were joined with the pump housing 100 in an orientation that is 180-degrees off from the selected orientation, the alignment tabs 132 would receive interference from the barrel channel 211 of the controller housing 210. As such, the user would be unable to attach the pump device 100 to the controller 200, thereby indicating to the user that the cap device 130 must be reoriented to the selected position.

Still referring to FIGS. 1-3, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (not shown in FIGS. 1-3) of the pump device 100. As described in more detail below, the pump device 100 includes a drive system that causes controlled dispensation of the medicine or other fluid from the cartridge 120. In some embodiments, the drive system incrementally advances a piston rod (not shown in FIGS. 1-3) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

In some embodiments, the controller device is configured to removably attach to the pump device 100 in a side-by-side arrangement. As such, the controller device 200 can be electrically connected with the pump device 100, while the controller device 200 remains outside of the pump housing 110 (and, likewise, the pump device 100 remains outside of the controller housing 210). Accordingly, the pump device 100 and the controller device 200 can be separate components that fit together, but the overall size of the combined assembly is reduced because there is no requirement for one component (e.g., the controller device) to completely surround or envelop the second component (e.g., the pump device). The compact size permits the infusion pump system 10 to be discrete and portable when the pump device 100 is attached with the controller device 200 (as shown in FIGS. 2-3). In this embodiment, the controller device 200 includes a controller housing structure 210 having a number of features (e.g., a barrel channel 211, a rail 212, a depression 213, and a guide channel 214a-b that is segmented by a release latch 215) that are configured to mate with complementary features (e.g., a barrel 111, a slider channel 112, an mating extension 113, and a segmented guide rail 114a-b) of the pump housing structure 110 so as to form a releasable mechanical connection (as shown, for example, in FIGS. 1 and 4-5). Such mating features of the pump housing structure 110 and the controller housing structure 210 can provide a secure connection in the previously described side-by-side arrangement. It should be understood that, in other embodiments, other features or connector devices can be used to facilitate the side-by-side mounting arrangement. These other features or connector devices may include, for example, magnetic attachment devices, mating tongues and grooves, or the like.

As shown in FIG. 1, the pump device 100 may include an electrical connector 118 (e.g., having conductive pads, pins, and the like) that are exposed to the controller device 200 and that mate with a complementary electrical connector (refer to connector 218 in FIG. 4) on the adjacent face of the controller device 200. The electrical connectors 118 and 218 provide the electrical communication between the control circuitry (refer, for example, to FIG. 15) housed in the controller device 200 and at least a portion of the drive system or other components of the pump device 100. For example, in some embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump system 10 may include a gasket 140 that provides a seal that is resistant to migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 includes a user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed (refer, for example, to FIG. 2). For example, the display 222 may be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. The user can also activate an illumination instrument 230 on the controller device 200 by pressing one or more buttons 224a, 224b, 224c, and 224d of the user interface 220.

The display 222 of the user interface 220 may be configured to display quick reference information when no buttons 224a, 224b, 224c, and 224d have been pressed. For example, as shown in FIG. 2, the active area of the display 222 can display the time and the date for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 222 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the user interface 220 of the controller device 200 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto).

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200, which is removably attached to the pump device 100, without the requirement of locating and operating a separate monitoring module.

In other embodiments, the user interface 200 is not limited to the display and buttons depicted in FIGS. 1-3. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 4:
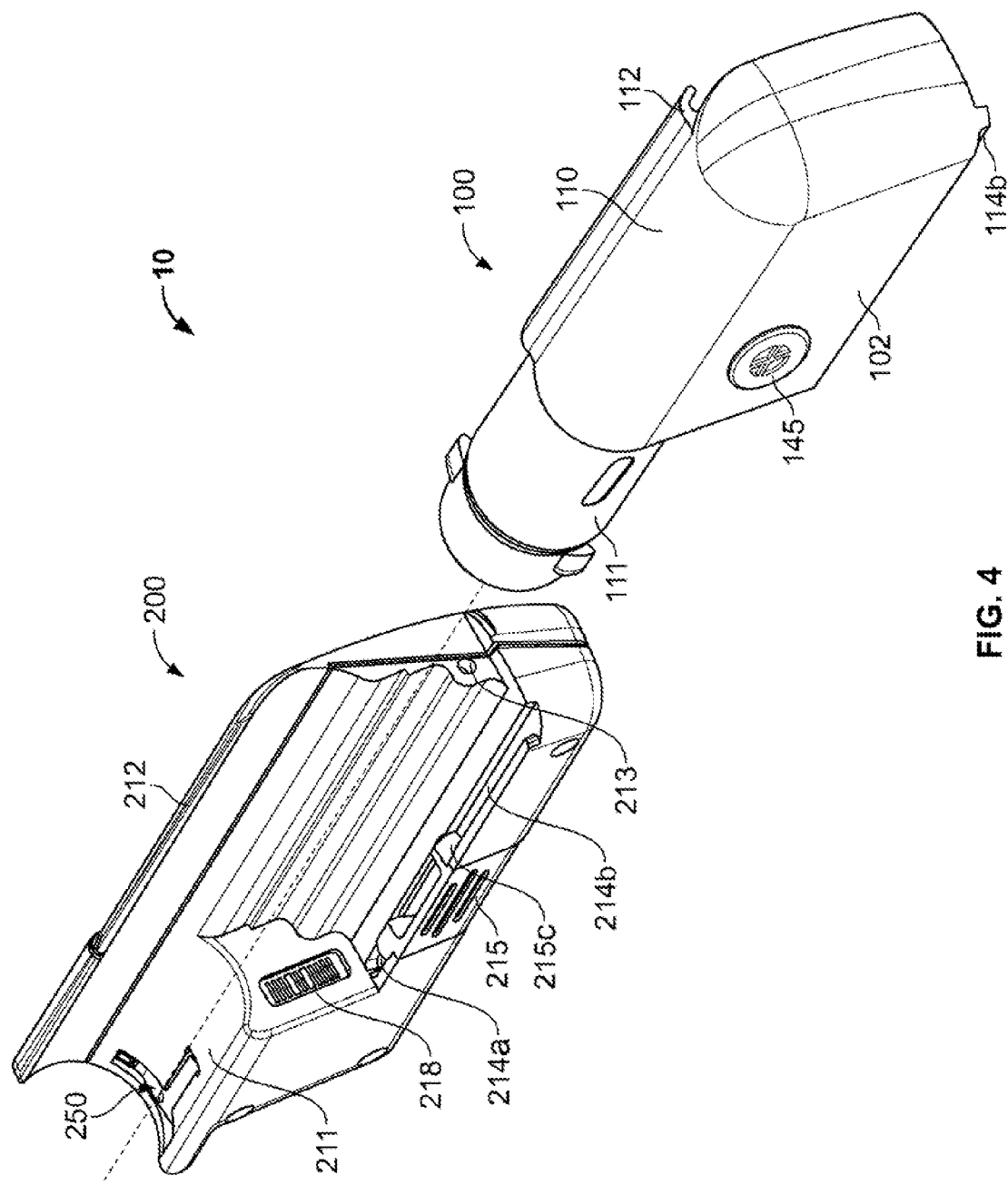
FIG. 4 is a perspective view of the infusion pump system of FIG. 1 in a detached state.
Figure 5:
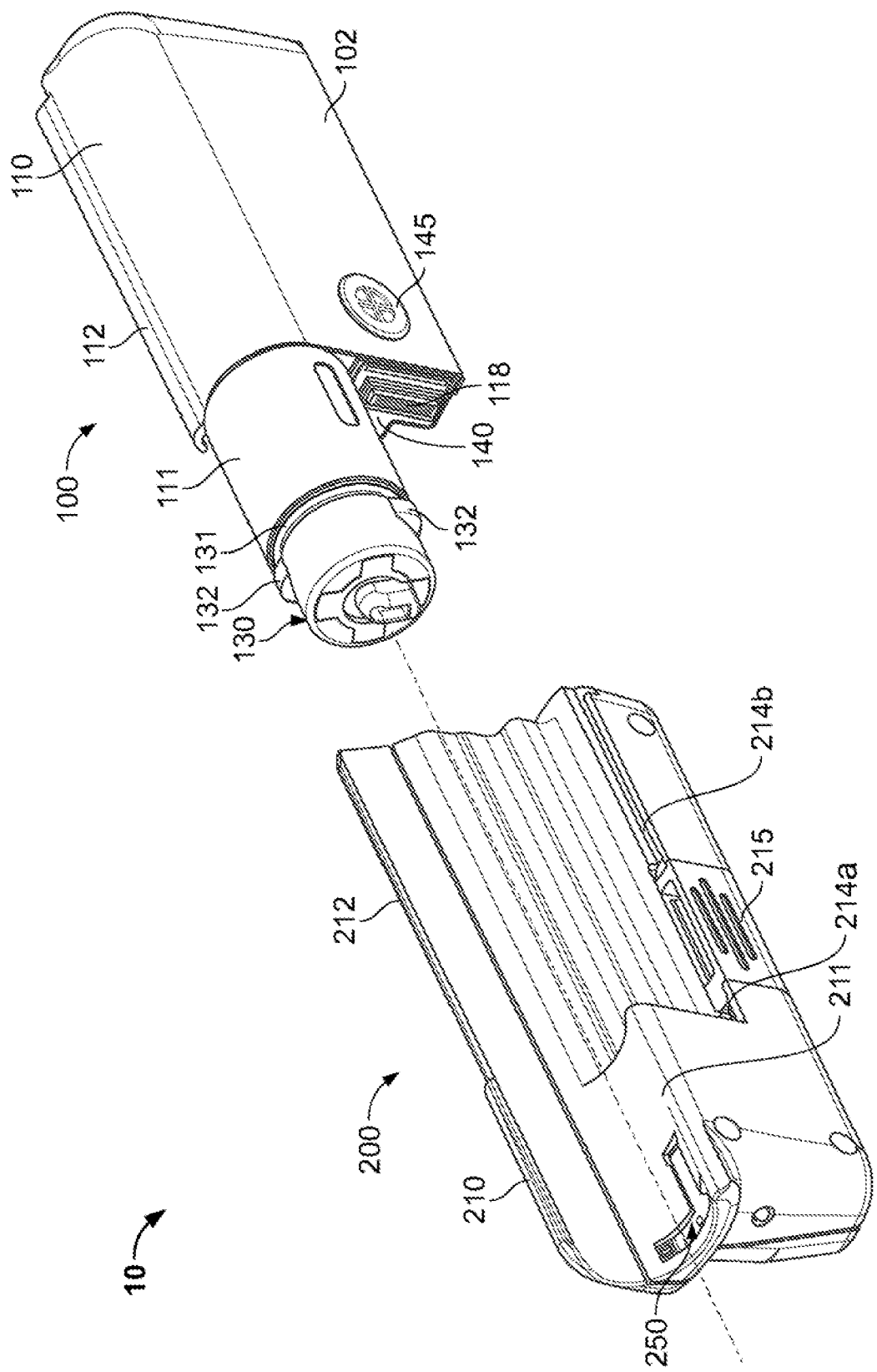
FIG. 5 is another perspective view of the infusion pump system on FIG. 4.

Referring now to FIGS. 4-5, when the infusion pump system 10 operates, the controller device 200 is removably attached to the pump device 100 in a side-by-side arrangement. For example, the pump device 100 may be moved in a longitudinal direction (e.g., refer to direction 219 in FIG. 13) toward the controller device 200 until the complementary features connect and secure the separate components in the side-by-side arrangement. In these circumstances, the pump device 100 and the controller device 200 can be separate components that fit together, but the overall size of the combined assembly is reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user (described in more detail below).

In this embodiment, the controller device 200 includes a controller housing structure 210 having a number of features that are configured to mate with complementary features of the pump housing structure 110 so as to form a releasable mechanical connection. For example, the pump housing structure 110 may include a barrel 111 that mates with a complementary barrel channel 211 of the controller housing 210. Also, the pump housing 110 includes slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 may include a segmented rail 114a-b (FIG. 1) that mates with a guide channel 214a-b to direct the relative longitudinal motion between the pump device 100 and the controller device 200. As described in more detail below, the segmented rails 114a-b may interact with the release member 215 so as to releasably secure the pump device 100 into assembly with the controller device 200. In addition, the pump housing 110 may include an extension 113 (FIG. 1) that mates with a depression 213 (FIG. 5) in the controller housing 210 when the pump device 100 is fully attached to the controller device 200.

Still referring to FIGS. 4-5, when the pump device 100 is advanced in the longitudinal direction toward the controller device 200 as guided by the slider channel 112 and the segmented rails 114a-b, the electrical connector 118 (FIG. 5) of the pump device 100 is directed toward engagement with the mating connector 218 (FIG. 4) of the controller device 200. As the connectors 118 and 218 join together to form the electrical connection, the release member 215 is shifted to a position between the segmented rails 114a-b so as to prevent withdrawal of the connection. Also, when the connectors 118 and 218 are mated, the extension 113 and barrel 111 are mated with the corresponding depression 213 and barrel channel 211 so as to resist relative rotational movement between the pump device 100 and the controller device 200. In this embodiment, the physical attachment of the electrical connectors 118 and 218 may also serve to resist relative rotational movement between the pump device 100 and the controller device 200. Furthermore, when the connectors 118 and 218 are mated, the slide channel 112 is mated with the corresponding rail 112 and barrel channel 211 so as to resist relative side-to-side movement between the pump device 100 and the controller device 200.

Accordingly, the pump device 100 is configured to removably attach to the controller device 200 in a manner that provides a secure fitting, an overall compact size, and a reliable electrical connection. When the pump device 100 and the controller device 200 are arranged in this side-by-side configuration, the controller device 200 can be electrically connected with the pump device 100 while the controller device 200 remains outside of the pump housing 110 (and, likewise, the pump device 100 remains outside of the controller housing 210). As such, the overall size of the assembled system 10 can be minimized, thereby providing an infusion pump system 10 having a discrete size and enhanced portability.

Additionally, in some embodiments, the attachment of the pump device 100 to the controller device 200 can be accomplished by a user with a convenient "one-movement" process. For example, as previously described, the user can readily slide the pump device 100 and the controller device 200 toward one another in a single movement (e.g., in the longitudinal direction) that causes both a physical connection and an electrical connection. As described in more detail below in connection with FIGS. 11-16, the release member 215 may be arranged so as to automatically adjust to a locked position when the pump device 100 is advanced into engagement with the controller device 200. Thus, the infusion pump system 10 permits users to readily join the pump device 100 and the controller device 200 without compound or otherwise difficult hand movements—a feature that can be beneficial to child users or to elderly users.

It should be understood that, in other embodiments, other features or connector devices can be used to facilitate the side-by-side mounting arrangement. These other features or connector devices may include, for example, magnetic attachment device, mating tongues and grooves, mounting protrusions that friction fit into mating cavities, or the like.

Still referring to FIGS. 4-5, the pump device 100 and the controller device 200 can be attached in a manner that is resistant to migration of external contaminants (e.g., water, dirt, and the like) both into the pump housing structure 110 and the controller housing structure 210. For example, when the pump device 100 is advanced in the longitudinal direction toward the controller device 200 (as guided by the slider channel 112 and the segmented rails 114a-b), the electrical connector 118 (FIG. 5) of the pump device 100 is directed toward engagement with the mating connector 218 (FIG. 4) of the controller device 200. When the connectors 118 and 218 join together to form the electrical connection, the gasket 140 is compressed between the adjacent surfaces of the pump housing 110 and the controller housing 210. The gasket 140 thereby forms a water-resistant seal between the ambient environment and the mated connectors 118 and 218.

The gasket 140 may comprise a polymer foam material that is adhered to a surface of either the pump housing 110 or the controller housing 210 (e.g., adhered to the pump housing 110 in this embodiment). The gasket 140 may be die cut to a selected shape so as to include an aperture for the electrical connection. Thus, in this embodiment, the gasket 140 surrounds the electrical connection when the pump device 100 is secured to the controller device 200. The configuration provides protection from water migration to one or both of the electrical connectors 118 and 218. Accordingly, in particular circumstances, the infusion pump system 10 can be assembled into a "water tight" configuration that protects sensitive internal components from water migration in the event that the user encounters water while wearing the pump system 10. In one example, the gasket 140 may resist migration of water to the electrical connectors 118 and 218 even when the system 10 is submerged underwater (e.g., in a pool, in a bath, or the like) for an extended period of time, such as at least 10 minutes, at least 30 minutes, at least one hour, at least two hours, and preferably at least four hours.

As shown in FIG. 5, the gasket 140 is arranged to extend generally perpendicular to the assembly motion when the pump device 100 is being attached to the controller device. For example, the pump device 100 can be attached to the controller device 200 by moving the pump device 100 in the longitudinal direction (e.g., refer to direction 219 in FIG. 13). The gasket 140 includes a major interface surface extends in a generally lateral direction that is perpendicular to the longitudinal assembly motion. Because the gasket 140 extends in a direction (e.g., the lateral direction in this embodiments) that is generally perpendicular to the attachment direction (the longitudinal direction in this embodiment), the gasket 140 can be sufficiently compressed to form a seal when the user performs the "one-movement" process to attach the pump device 100 and the controller device 200.

In addition, other paths for migration of external contaminants into the assembled pump system 10 may be sealed. For example, the infusion pump system 10 may include one or more seals that are arranged to hinder migration of external contaminants between the cap device 130 and the pump housing 110 into the cavity 116 of the pump device 100. In this embodiment, the seal 131 arranged between the cap device 130 and the barrel 111 can provide an effective water-resistant seal against water migration into the cavity. As such, the medicine cartridge 120 and pump drive system (not shown in FIGS. 4-5) can be protected during operation.

Still referring to FIGS. 4-5, some embodiments of the infusion pump system 10 may employ a power source arranged in pump device 100 or the controller device 200 that draws upon surrounding air for optimum operation. Because the controller device 200 and the pump device 100 may be sealed to resist water migration during normal usage, a water-resistant vent instrument 145 may be used to provide the air to the power source without permitting migration of water therethrough. For example, in this embodiment, the pump device 100 may house a power source 345 in the form of a zinc-air cell battery (refer to FIG. 18), which draws upon the surrounding air during operation. When the pump device 100 is in use, the pump housing 110 is preferably sealed to protect the internal drive system and medicine cartridge from water migration. As such, the pump housing 110 may include a water-resistant vent instrument 145 disposed proximate to the zinc-air cell battery 345 so that some air may pass through the vent 145 and toward the battery. The water-resistant vent instrument 145 may include one or more layers of a material that is permeable to air and resistant to passage of liquids such as water. For example, the water-resistant vent instrument 145 may include one or more layers of a GORE-TEX material to resist the migration of water into the pump device while permitting the passage of air toward the battery.

Accordingly, the pump device 100 and the controller device 200 can be mounted to one another so that the assembled system 10 is resistant to water migration both into the pump housing structure 110 and the controller housing structure 210. Such a configuration may also provide water-resistant protection for the electrical connection between the pump device 100 and the controller 200. Thus, the sensitive internal components in the controller device 200 and the pump device 100 can be reliably protected from water migration if the user encounters water (e.g., rain, incidental splashing, and the like) while using the pump system 10.

Figure 6:
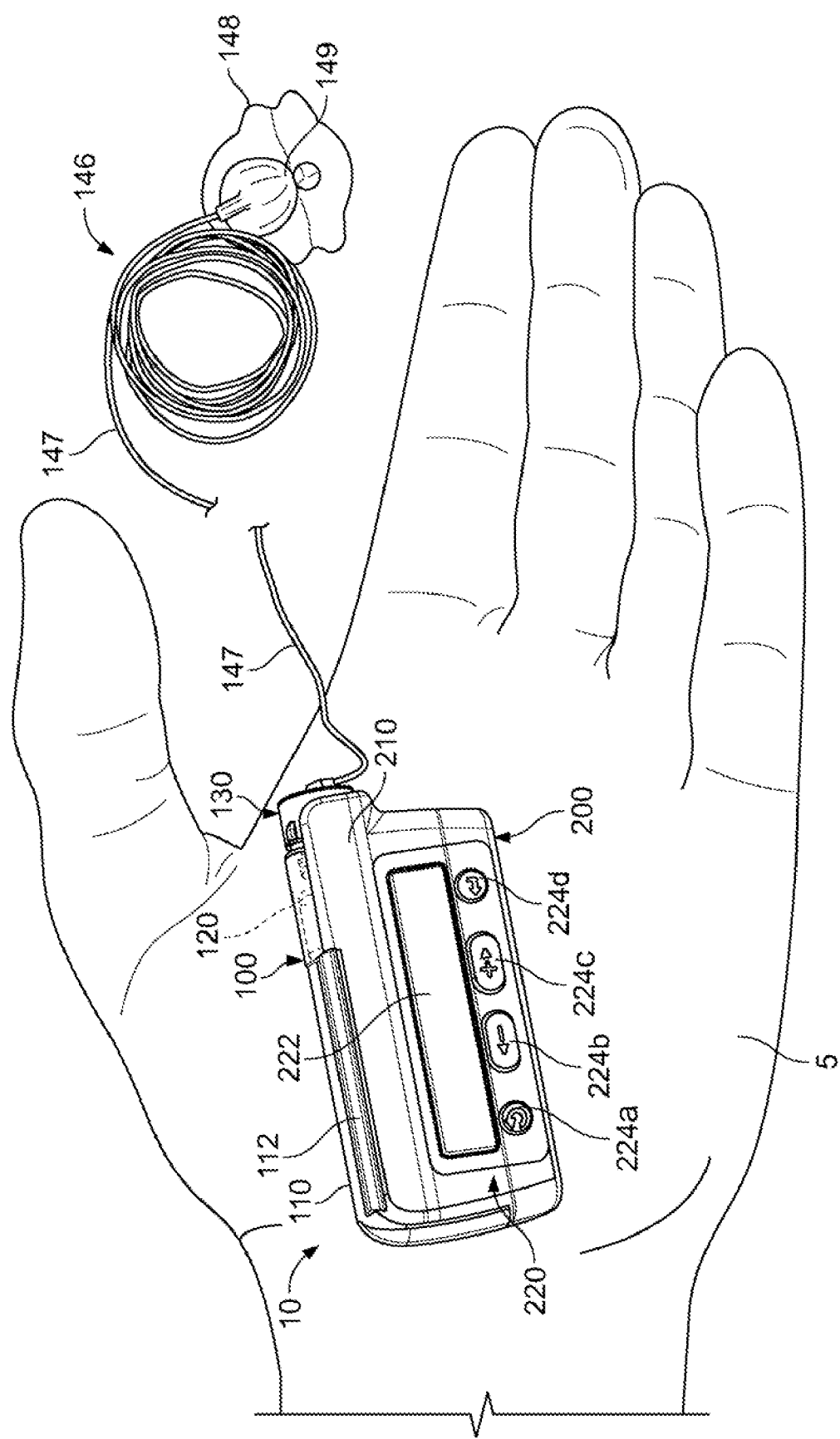
FIG. 6 is a perspective view of an infusion pump system, in accordance with some embodiments.
Figure 7:
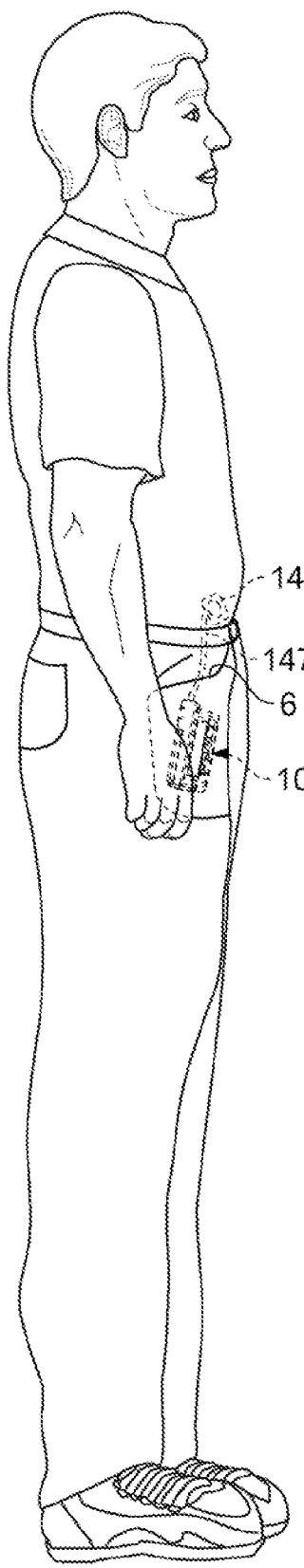
FIG. 7 is a perspective view of the infusion pump system of FIG. 6 worn on clothing of a user.
Figure 8:
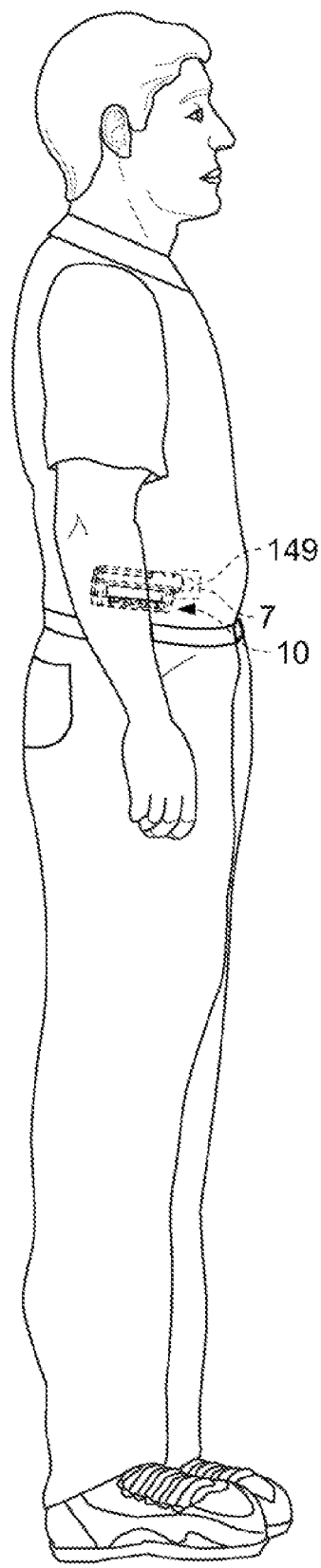
FIG. 8 is a perspective view of an infusion pump system worn on skin of a user, in accordance with particular embodiments.

Referring to FIGS. 6-8, the infusion pump system 10 may be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The drive system of the pump device 100 may be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in one embodiment). In addition, the pump housing structure 110 may have an overall height of about 2 cm to about 4 cm (about 3.1 cm or less in one embodiment) and an overall thickness of about 8 mm to about 20 mm (about 17.5 mm or less in one embodiment). In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump system 10 (including the removable controller device 200 attached to the pump device 100 having the cap 130) may have an overall length of about 7 cm to about 10 cm (about 9.3 cm or less in one embodiment), an overall height of about 2 cm to about 5 cm (about 4.2 cm or less in one embodiment), and an overall thickness of about 8 mm to about 20 mm (about 17.5 mm or less in one embodiment).

The pump system 10 is shown in FIG. 6 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with an infusion set 146. In general, the infusion set 146 is tubing system that connects the infusion pump system 10 to the tissue or vasculature of the user (e.g., to deliver medicine into the tissue or vasculature under the user's skin). The infusion set 146 may include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 may provide fluid communication between the output end 122 (FIG. 1) of the medicine cartridge 120 and the tube 147 of the infusion set 146. For example, the tube 147 may be directly connected to the output port 139 (FIG. 1) of the cap device 130. In another example, the infusion set 146 may include a connector (e.g., a Leur connector or the like) attached to the tube 147, and the connector can then mate with the cap device 130 to provide the fluid communication to the tube 147. In these examples, the user can carry the portable infusion pump system 10 (e.g., in the user's pocket, connected to a belt clip, adhered to the user's skin, or the like) while the tube 147 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module (refer for example to FIG. 6).

Referring to FIG. 7, in some embodiments, the infusion pump system 10 is pocket-sized so that the pump device 100 and controller device 200 can be worn in the user's pocket 6 or in another portion of the user's clothing. For example, the pump device 100 and the controller device 200 can be attached together and form the system that comfortably fits into a user's pocket 6. The user can carry the portable infusion pump system 10 and use the tube 147 of the infusion set 146 extends to direct the dispensed medicine to the desired infusion site. In some circumstances, the user may desire to wear the pump system 10 in a more discrete manner. Accordingly, the user may pass the tube 147 from the pocket 6, under the user's clothing, and to the infusion site where the adhesive patch 148 is positioned. As such, the pump system 10 can be used to delivery medicine to the tissues or vasculature of the user in a portable, concealable, and discrete manner.

Referring to FIG. 8, in other embodiments, the infusion pump system 10 may be configured to adhere to the user's skin 7 directly at the location in which the skin is penetrated for medicine infusion. For example, a rear surface 102 (FIG. 3) of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 149 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220.

Referring now to FIGS. 9-14, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days-depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 9-10, the pump device 100 can be readily removed from the controller device 200 when the medicine cartridge 120 is exhausted. As previously described, the medicine cartridge 120 is inserted into the cavity 116 (FIG. 1) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length. Optionally, some embodiments of the pump device 100 may include a label 117a that is adhered around the barrel 111. The label 117a may provide a convenient location for basic user instructions, product identification information, and other information related to the infusion pump system 10. To provide enhanced viewability of the medicine cartridge 120 through the label 117a, the label 117a may include a window 117b through which the user may visually inspect if the plunger 125 is nearing the end of its travel length.

As shown in FIG. 9, the pump device 100 has been used to a point at which the medicine cartridge 120 is exhausted. The plunger 125 has been advanced, toward the left in FIG. 9, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 (and through the window 117b of the label 117a in this embodiment) to determine if the medicine cartridge 120 is almost empty. When the user determines that a new medicine cartridge 120 should be employed, the pump device 100 can be readily separated from the controller device 200 by actuating the release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 9) away from the pump device 100 (e.g., by applying a force with the user's finger).

As shown in FIG. 10, when the release member 215 is actuated and moved to a position away from the pump device 100, the segmented guide rail 114a-b is free to slide longitudinally in the guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 1) may be withdrawn from the mating depression 213 (FIG. 10), and the electrical connector 118 can be separated from the mating connector 218. In these circumstances, the pump device 100 is physically and electrically disconnected from the controller device 200, while the pump device retains the exhausted medicine cartridge 120.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., move in the lateral direction 216 in the embodiment shown in FIG. 9). Accordingly, in some embodiments, the pump device 100 can automatically and sharply move a small distance (e.g., about 0.5 mm to about 5 mm) away from the controller 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Referring to FIGS. 11-12, the same controller device 200 can be reused with a new pump device 100' having a new medicine cartridge 120' retained therein, and the previously used pump device 100 can be discarded with the exhausted medicine cartridge 120. The new pump device 100' (FIG. 11) can have a similar appearance, form factor, and operation as the previously used pump device 100 (FIGS. 9-10 and 12), and thus the new pump device 100' can be readily attached to the controller device 200 for controlled dispensation of medicine from the new medicine cartridge 120'. In some embodiments, the user may prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 11, it should be understood that the tubing 147 may be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller 200) before attaching the infusion set patch to the user's skin. As shown in FIG. 11, the new medicine cartridge 120' may be filled with medicine such that the plunger 125 is not viewable through the barrel 111.

As shown in FIG. 12, the previously used pump device 100 that was separated from the controller device (as described in connection with FIGS. 9-10) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 20, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 146 (not shown in FIG. 12, refer to FIG. 8) that was used with the pump device 100 may be removed from the user and discarded into the bin 20 along with the pump device 100. Alternatively, the infusion set 146 can be disconnected from the previous pump device 100 and attached to the new pump device 100'. In these circumstances, the user may detach the infusion set cannula and patch from the skin so as to "re-prime" the tubing with medicine from the new pump device 100' to remove air pockets from the tubing. Thereafter, the infusion set cannula and patch can be again secured to the user's skin.

Referring to FIGS. 13-14, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. In this embodiment, the new pump device 100' includes the removable tab 141 to seal the battery in the unused pump device 100' and thereby maintain the battery in a storage mode (refer, for example, to FIG. 12 in which the removable tab 141 is arranged to cover an internal face of the vent 145. As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

The new pump device 100' can be connected to the controller device 200 by advancing the new pump device 100' in a longitudinal direction 219 (FIG. 13) toward the controller device 200. When the pump device 100' is advanced in the longitudinal direction 219 toward the controller device 200, the movement is guided by the slider channel 112 (FIGS. 4-5) and the segmented rails 114a-b. In particular, the slider channel 112 of the pump housing engages the rail 212 of the controller housing 210. Also, the front portion of the segmented rail 114a slides into the rear portion of the guide channel 214b. In this embodiment, the front portion of the segmented rail 114a includes a ramp surface 114c (refer also to FIG. 1) that engages a complementary ramp surface 215c (FIG. 4) of the release member 215 to thereby force the release member 215 away from the guide channel 214a-b during advancement of the pump device 100'. The release member 215 is temporarily forced away from the guide channel 214a-b so that the front portion of the segmented rail 114a passes over the release member 215, which enables the electrical connector 118 of the pump device 100' to engage with the mating connector 218 of the controller device 200. As the connectors 118 and 218 join together to form the electrical connection, the release member 215 biased to return to its latched position and is shifted to a position in the guide channel 214a-b between the segmented rails 114a-b so as to prevent withdrawal of the pump device 100'.

Also, when the connectors 118 and 218 are mated, the extension 113 (FIG. 1) and barrel 111 are mated with the corresponding depression 213 and barrel channel 211 so as to resist relative rotational movement between the pump device 100 and the controller device 200. In this embodiment, the physical attachment of electrical connectors 118 and 218 may also serve to resist relative rotational movement between the pump device 100 and the controller device 200. Furthermore, when the connectors 118 and 218 are mated, the slide channel 112 is mated with the corresponding rail 112 (FIG. 1) and barrel channel 211 so as to resist relative side-to-side movement between the pump device 100 and the controller device 200.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 permits users to readily join the pump device 100' and the controller device 200 without compound or otherwise difficult hand movements—a feature that can be beneficial to child users or to elderly users.

As shown in FIG. 14, when the new pump device 100' is fully advanced and attached to the controller device 200, the gasket 140 is compressed between the opposing surfaces of the pump housing 110 and the controller housing 210. Such a configuration provides a water-resistance seal around the electrical connection that protects the sensitive internal components of the pump device 100' and the controller device 200 from damage or malfunction. Although the tubing 147 of the infusion set 146 is not shown in FIGS. 13-14, it should be understood that the tubing 147 may be attached to the cap device 130 to provide a fluid path from the new pump device 100' to the user.

Accordingly, the new pump device 100' can removably attach to the controller device 200 in a manner that provides a secure fitting, an overall compact size, and a reliable electrical connection. When the pump device 100' and the controller device 200 are arranged in this side-by-side configuration, the controller device 200 can be electrically connected with the pump device 100' while the controller device 200 remains outside of the pump housing 110 (and, likewise, the pump device 100 remains outside of the controller housing 210). As such, the overall size of the assembly system 10 can be minimized, thereby providing an infusion pump system having a discrete size and enhanced portability.

Figure 15:
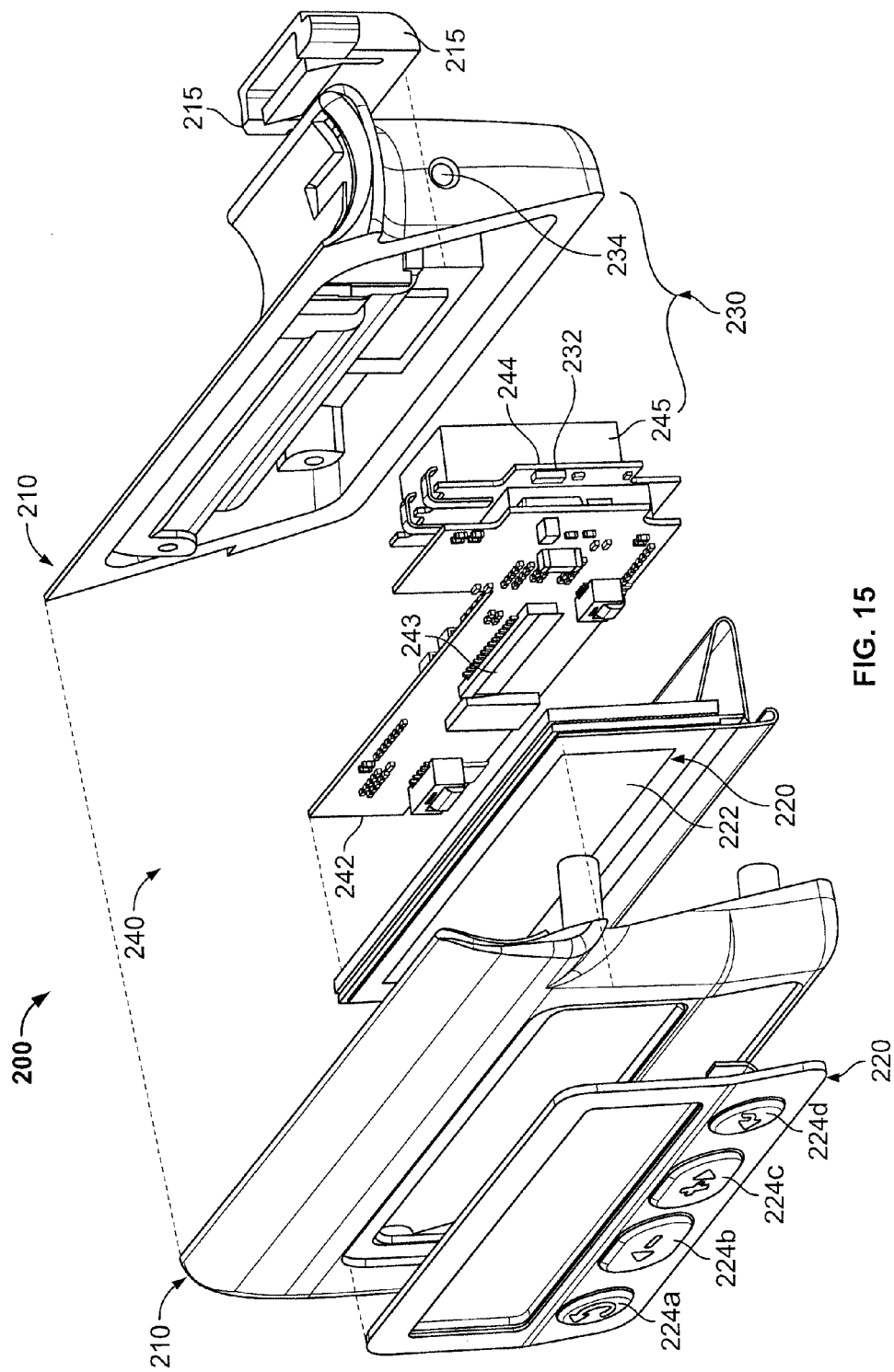
FIG. 15 is an exploded perspective view of a controller device for an infusion pump system, in accordance with some embodiments.

Referring now to FIG. 15, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the memory devices arranged in the control circuitry 240. Furthermore, the control circuitry 240 may include one or more dedicated memory devices that store executable software instructions for the processor 243. The control circuitry 240 may include other components, such as sensors, that are electrically connected to the main processor board 242. For example, at least a portion of the occlusion sensor system 250 (not shown in FIG. 15) can be electrically connected to the main processor board 242 via a flexible circuit substrate or one or more wires, as described in more detail below in connection with FIG. 19.

The controller device 200 can be electrically connected with the pump device 100 via mating connectors 118 and 218 (FIGS. 4-5) so that the control circuitry 240 can communicate control signals to the pump device 100 and receive feedback signals from components housed in the pump device 100. In this embodiment, the electrical connector 118 (FIG. 5) on the pump device 100 is a z-axis connector, and the connector 218 (FIG. 4) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Also as previously described, the controller device 200 can include the illumination instrument 230 that may be operated by the controller circuitry 240. For example, the illumination instrument 230 can include an LED device 232 that is electrically activated by the control circuitry 240 according to the user's input or according to the previously described automated conditions. The light emitted from the LED device 232 can be transmitted through a light guide 234 arranged on the external face of the controller housing 210. It should be understood that, in other embodiments, the illumination instrument 230 may include other light source configurations.

Still referring to FIG. 15, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of settings or menu options for the infusion pump system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port or another data cable port) that is accessible on an external portion of the controller housing 210. As such, a cable may be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Still referring to FIG. 15, the control circuitry 240 of the controller device 200 may include a second power source 245 that can receive electrical energy from a first power source 345 (FIG. 16) housed in the pump device 100. In this embodiment, the second power source 245 is coupled to the power supply board 244 of the control circuitry 240. The hard-wired transmission of the electrical energy can occur through the previously described connectors 118 and 218 (FIGS. 4-5). In such circumstances, the first power source 345 (FIG. 16) may include a high density battery that is capable of providing a relatively large amount of electrical energy for its package size, while the second power source 245 (FIG. 15) may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, as previously described, the first battery 345 may comprise a zinc-air cell battery. The zinc-air cell battery 345 may have a large volumetric energy density compared to some other battery types. For example, the zinc-air cell battery 345 may have a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery may have a long storage life, especially in those embodiments in which the battery is sealed (e.g., by the removable tab 141 or the like) during storage and before activation. One exemplary zinc-air cell battery provides a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA·h (about 650 mA·h in one embodiment).

As shown in FIG. 15, the second battery 245 may include a high current-output device that is housed inside the controller housing 210. The second battery 245 can be charged over a period of time by the first battery 345 and then intermittently deliver high-current bursts to the drive system 300 over a brief moment of time. For example, the second battery 245 may comprise a lithium-polymer battery. The lithium polymer battery disposed in the controller device 200 may have an initial current output that is greater than the zinc-air cell battery disposed in the pump device 100, but zinc-air cell battery may have an energy density that is greater than the lithium polymer battery (e.g., the lithium polymer battery disposed in the controller device 200 may have a volumetric energy density of less than about 600 Wh/L). In addition, the lithium-polymer battery 245 is readily rechargeable, which permits the zinc-air battery 345 disposed in the pump device 100 to provide electrical energy to the lithium-polymer battery 245 for purposes of recharging. One exemplary lithium-polymer battery provides a initial current output of about greater than 80 mA (about 90 mA to about 110 mA, and about 100 mA in one embodiment) and a maximum potential voltage of about 4.0V to and 4.4V (about 4.2 V in one embodiment). In other embodiments, it should be understood that the second power source 245 may comprise a capacitor device capable of being recharged over time and intermittently discharging a current burst to activate the drive system 300.

Accordingly, the infusion pump system 10 having two power sources 345 and 245—one arranged in the pump device 100 and another arranged in the reusable controller device 200—permits a user to continually operate the controller device 200 without having to recharge a battery via a wall-plug or other cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Figure 16:
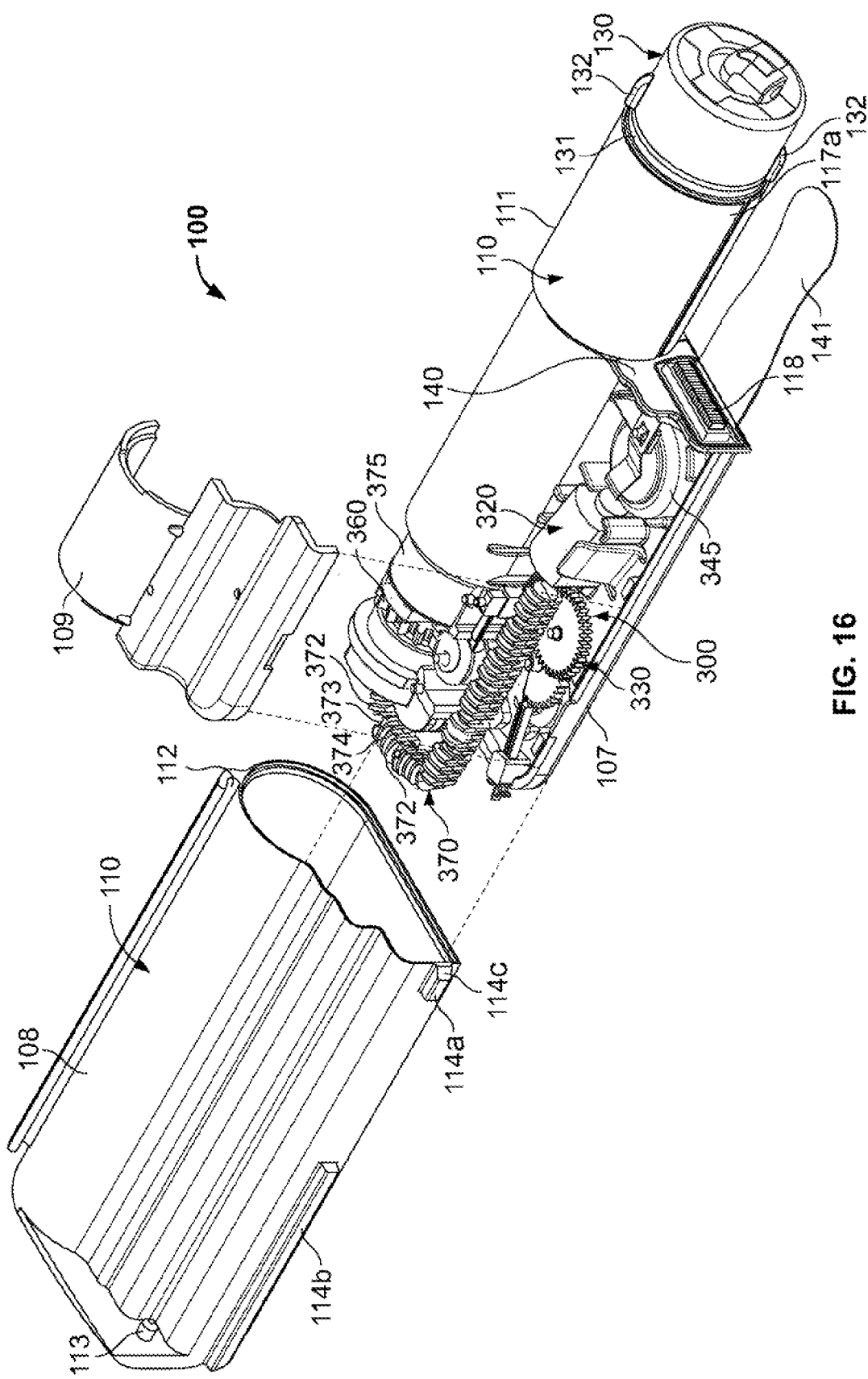
FIG. 16 is an exploded perspective view of a pump device for an infusion pump system, in accordance with some embodiments.
Figure 17:
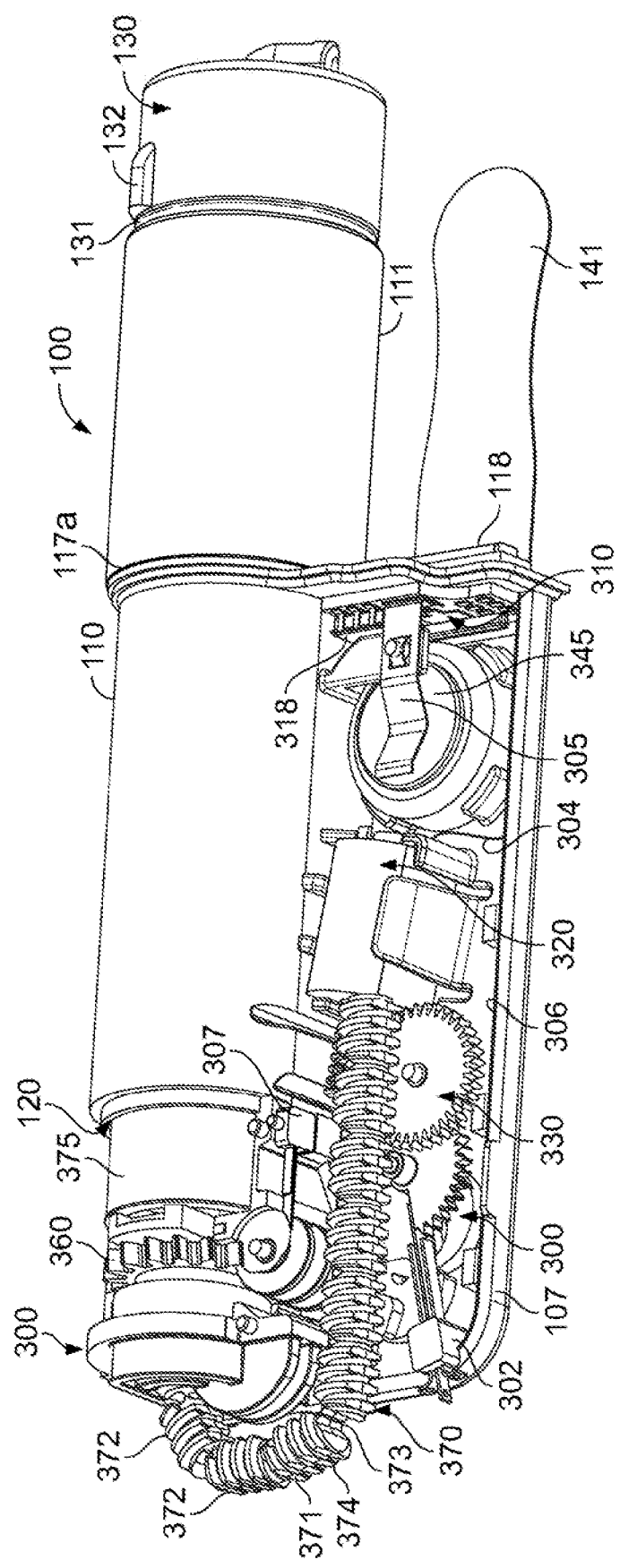
FIG. 17 is a perspective view of a portion of the pump device of FIG. 16.
Figure 18:
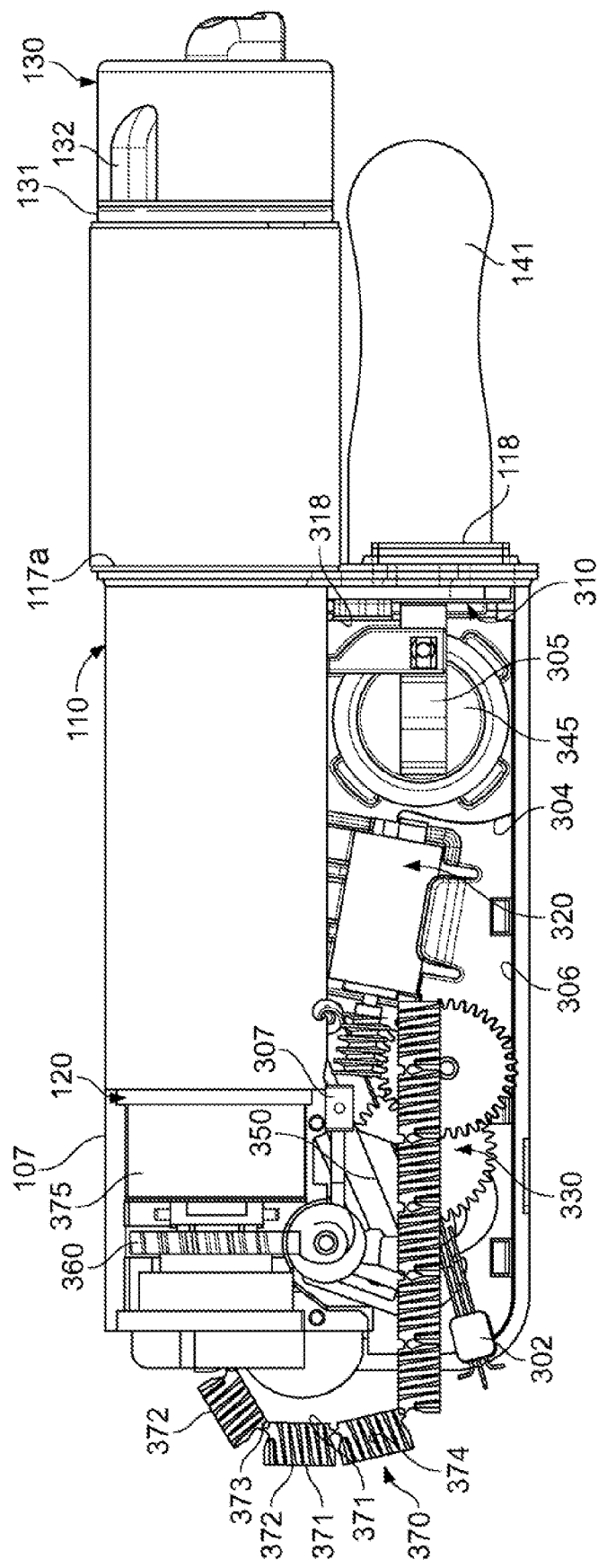
FIG. 18 is a top view of a portion of the pump device of FIG. 16.
Figure 19:
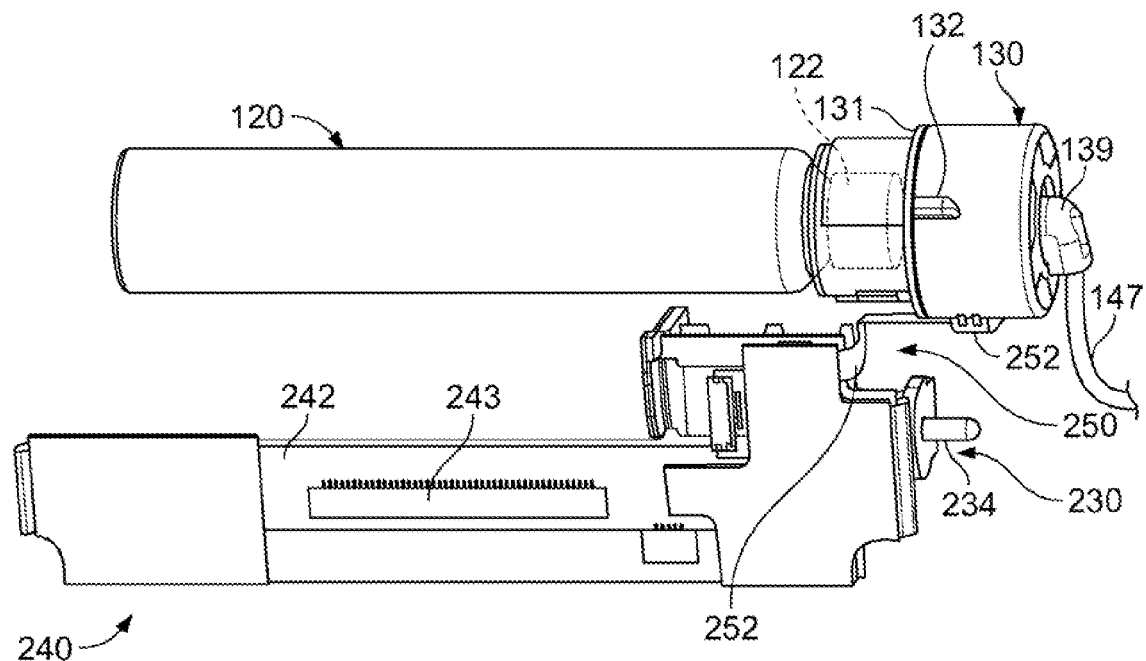
FIG. 19 is a perspective view of occlusion sensor circuitry from a controller device arranged adjacent to a cap of a pump device, in accordance with some embodiments.

Referring now to FIGS. 16-18, the pump device 100 may include a drive system 300 that is controlled by the removable controller device 200 (FIGS. 1-5). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. In this embodiment, the pump housing 110 includes a chassis 107, a shell portion 108, and a cover mount 109. The shell portion 108 can be used to cover at least a portion of the drive system 300. For example, the shell 108 may include an inner curved surface against which a curved section of a piston rod 370 rests. The cover mount 109 may be assembled to the chassis 107 of the pump housing 110 to secure some components of the drive system 300 in position between the cover mount 109 and the chassis 107. When the cover mount 109 is assembled into place, the "unused" or retracted portion of the piston rod 370 may rest in a channel defined in the top of the cover mount 109. The shell portion 108 can slide over the cover mount 109 and join with the chassis 107 to form the assembled pump housing 110.

Some embodiments of the drive system 300 may include a battery powered actuator (e.g., reversible motor 320 or the like) that resets a ratchet mechanism 330, a spring device 350 that provides the driving force to the ratchet mechanism 330, and a drive wheel 360 that is rotated by the ratchet mechanism 330 to advance the flexible piston rod 370 toward the medicine cartridge 120. The operation of the drive system 300 is described in commonly assigned U.S. patent application Ser. No. 11/677,706, which was filed on Feb. 22, 2007 and is incorporated herein by reference.

As shown in FIGS. 17-18, the pump device 100 can include one or more motion detectors coupled with the drive system 300 to provide feedback regarding the operation of the drive system 300. For example, the pump device 100 may include a first motion detector 302 configured as a limit switch that detects when a portion of the ratchet mechanism has reached the limit of its travel and must thereafter stop movement or reverse direction. The operation of the limit switch 302 is described in previously incorporated U.S. patent application Ser. No. 11/677,706. In another example, the pump device 100 may include a second motion detector 307 in the form of a mechanical error switch that indicates whether components of the drive system 300 completed the desired motion for each drive cycle. The operation of the mechanical error switch 307 is also described in more detail in U.S. patent application Ser. No. 11/677,706.

Referring to FIGS. 17-18, the pump device 100 includes a connector circuit 310 to facilitate the transfer of signals to and from the electrical connector 118. As previously described, the electrical connector 118 of the pump device 100 mates with the connector 218 (FIG. 4) of the controller device 200 so that electrical communication can occur between the pump device 100 and the controller device 200. The connector circuit 310 may comprise a generally non-complex circuit 310 that does not include a processor or other relatively high-cost components. In this embodiment, the connector circuit 310 operates as a passageway for the control signals (from the control circuitry 240 (FIG. 15) of the controller device 200) to transmit to the drive system 300 (e.g., to the actuator 320). For example, the reversible motor 320 may be connected to the connector circuit 310 via one or more wires 304. The connector circuit 310 also operates as a passageway for the electrical power from the first battery 345 (FIG. 17) to pass to the controller device 200 for recharging of the second battery 245 (FIG. 15). For example, the first battery 345 may be connected to the connector circuit 310 via one or more power contacts 305. Furthermore, the connector circuit 310 operates as a passageway for feedback signals (e.g., from the motion detectors 302 and 307) to transmit to the control circuitry 240 (FIG. 15) of the controller device 200. For example, the limit switch 302 may be connected to the connector circuit 310 via one or more wires 306 (the one or more wires connecting the mechanical error switch 307 to the connector circuit 310 are not shown in FIGS. 17-18).

In some embodiments, the connector circuit 310 in the pump device 100 includes a memory device 318 that can store data regarding the pump device 100 and its operational history. For example, the memory device 318 of the connector circuit 310 may include a flash memory chip that is configured to store data such as: a unique serial number designated for the pump device 100, a manufacturer identifier code, and a drive cycle counter. The unique serial number designated for the pump device 100 and the manufacturer identifier code may be useful pieces of quality control information that remains with the pump device 100 throughout its shelf-life and operational life. If, for example, a manufacturing error is identified for a particular pump device 100, the unique serial number and the manufacturer identifier code (e.g., a lot code) can be used to promptly identify the manufacturing location and its manufacturing lot.

The drive cycle counter stored in the memory device 318 can be useful for maintaining an accurate estimate of the volume of medicine that remains in the medicine cartridge 120. For example, the number of drive cycles that are required to incrementally advance the plunger 125 and thereby dispense a full medicine cartridge 120 may be a predetermined value (e.g., in some embodiments, 6,300 drive cycles result in full dispensation of a new medicine cartridge). Accordingly, the drive cycle counter stored in the memory device 318 can keep track of the number of drive cycles that have occurred through the operational life of the pump device 100. Each time the motor 320 completes a new drive cycle and incrementally advances the piston rod 370 to dispense some medicine, the controller device 200 can store an updated value for the drive cycle counter stored in the memory device 318. When the updated value stored in drive cycle counter stored in the memory device 318 approaches the predetermined value, the controller device 200 can alert the user that the medicine cartridge is approaching exhaustion. Furthermore, because the memory device 318 is arranged in the pump device 100, the drive cycle counter stored in the memory device 318 remains local to the pump device 100. If the pump device 100 is temporarily disconnected from the controller device 200 and then reconnected (or reconnected to a different controller device 200), the controller device 200 can retrieve the value for the drive cycle counter stored in the memory device 318 and promptly ascertain how much medicine remains in the medicine cartridge 120.

Still referring to FIGS. 17-18, in some embodiments, the flexible piston rod 370 comprises a plurality of segments 372 serially connected by hinge portions 373 so that the flexible piston rod 370 is adjustable from a curved shape to a non-curved shape. The plurality of segments 372 and the interconnecting hinge portions 373 can be integrally formed in one piece from one or more moldable materials, including polymer materials such as Nylon or POM. In this embodiment, each of the plurality of rod segments 372 includes an exterior thread pattern 374 along at least one cylindrical surface portion. The piston rod 370 also includes a plunger engagement device 375 can be arranged at a forward end of the piston rod 370. As such, the plunger engagement device 375 faces toward the medicine cartridge 120 when the medicine cartridge 120 is inserted into the cavity 116. In some embodiments, the plunger engagement device 375 may comprise a pusher disc that abuts against the plunger 125 of the medicine cartridge 120 (FIG. 1).

In some embodiments, the flexible piston rod 370 can include an anti-rotation structure that hinders the piston rod 370 from rotating with the drive wheel 360 (thereby allowing the rotation of the drive wheel 360 to translate into a longitudinal motion of the piston rod 370). For example, as shown in FIGS. 17-18, the flexible piston 370 includes longitudinal flat surfaces 371 extending along each of the segments 372. The longitudinal flat surfaces 371 can engage a complementary surface on the pump housing 110 (not shown in FIGS. 17-18) proximate the drive wheel 360 so that the flexible piston rod 370 is hindered from rotating when the drive wheel 360 turns. Accordingly, the longitudinal flat surfaces 371 on each segment 372 align to form a key that is received in a mating keyway (e.g., a complementary flat surface) on the pump housing. In other embodiments, the anti-rotation structure may include one or more longitudinal channels (with each channel capable of engaging an associated protrusion that acts as a key to hinder rotation while permitting longitudinal motion) or the like.

Because the flexible piston rod 370 is adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. The pump device 100 incorporating the flexible piston rod 370 can require less space than a similar device that houses a non-flexible, rigid rod.

Accordingly, in these embodiments, the piston rod 370 may undergo only forward or positive longitudinal displacement as a result of drive system 300. For example, the drive system 300 substantially hinders the piston rod 370 from retracting or "backing up" in response to fluid pressure in the medicine cartridge 120 or other reversal forces. In such circumstances, the flexible piston rod 370 can be retracted only upon manual disassembly of the pump device 100 (e.g., to disengage the drive gear 360 or the ratchet mechanism 330). In those embodiments in which the pump device 100 is intended to be disposable and non-reusable, the non-retractable piston rod configuration may facilitate a "one time use" disposable pump device by hinder attempts to insert a new medicine cartridge 120 in a previously used pump device 100. Such a configuration can thereby reducing the likelihood of failure due to non-intended repeated use of the disposable pump device 100. In one example, the drive system 300 can advance the piston rod 370 a longitudinal increment distance of about 16 microns or less (about 4 microns to about 12 microns, about 5 microns to about 9 microns, and preferably about 6 microns to about 8 microns) for each incremental motion cycle of the ratchet mechanism 330.

Moreover, the reversible rotation of the motor 320 may provide enhanced safety. As previously described, each drive cycle (including the reset step and the drive step) includes rotation of the motor 320 in a first direction and subsequent rotation in a second opposite direction. Thus, in certain embodiments, if a short-circuit or other malfunction of the motor 320 causes continuous rotation of the motor 320 in one direction, such a malfunction does not result in continuous dispensation (e.g., a possible over dosage) of medicine to the user. Accordingly, the drive system 300 can be reliably operated to dispense the selected dosages of medicine.

Referring now to FIGS. 19-31, the infusion pump system 10 can be equipped with an occlusion sensor system 250 that detects occlusions in the fluid flow path extending to the user. With specific reference to FIGS. 19 and 20, the occlusion sensor system 250 operates to detect changes in the flow path from the pump device 100 (e.g., through the cap device 130).

The occlusion sensor system 250 may include a number of components that are arranged in the controller device 200 and others that are arranged in the cap device 130. For example, a sensor circuit 252 is at least partially housed in the controller device 200 and operates in conjunction with a flow sensor device 400 that is arranged in a chamber 402 of the cap device 130. Accordingly, the sensor circuit 252 may be reused along with the controller device 200, while the flow sensor device 400, which may include relatively low-cost components, in the pump device 100 are discarded after the "one time use" of the pump device 100. The sensor circuit 252 can be arranged so that the cap device 130 is aligned with the components of the sensor circuit 252 when the pump device 100 is attached to the controller device 200, as described in more detail below. It should be understood that the pump housing 110 and the controller housing 210 have been removed from FIG. 19 for purposes of showing the relative position of the sensor circuit 252 (in the controller device 200 as shown in FIGS. 4-5) and the cap device 130 (attached to the pump housing 110 as shown in FIG. 4-5).

The sensor circuit 252 can be connected to the control circuitry 240 of the controller device 200 (FIG. 15) via a flexible circuit substrate or one or more wires. In this embodiment, the sensor circuit 252 connects with the main processor board 242 via a flexible circuit substrate. As such, the control circuitry 240 can receive sensor signals and employ detection software stored in one or more memory devices to determine if an occlusion exists. More specifically, the absence or presence of fluid flow can be determined by the detection software in response to the sensor signals. If the sensor signals from occlusion sensor system 250 indicate that an occlusion exists and there is either no fluid flow or limited fluid flow, the controller device 200 can trigger an alert to inform the user. The alert may include a visual alarm communicated via the user interface 220 of the controller device 200, an audible alarm, or a combination thereof.

Figure 20:
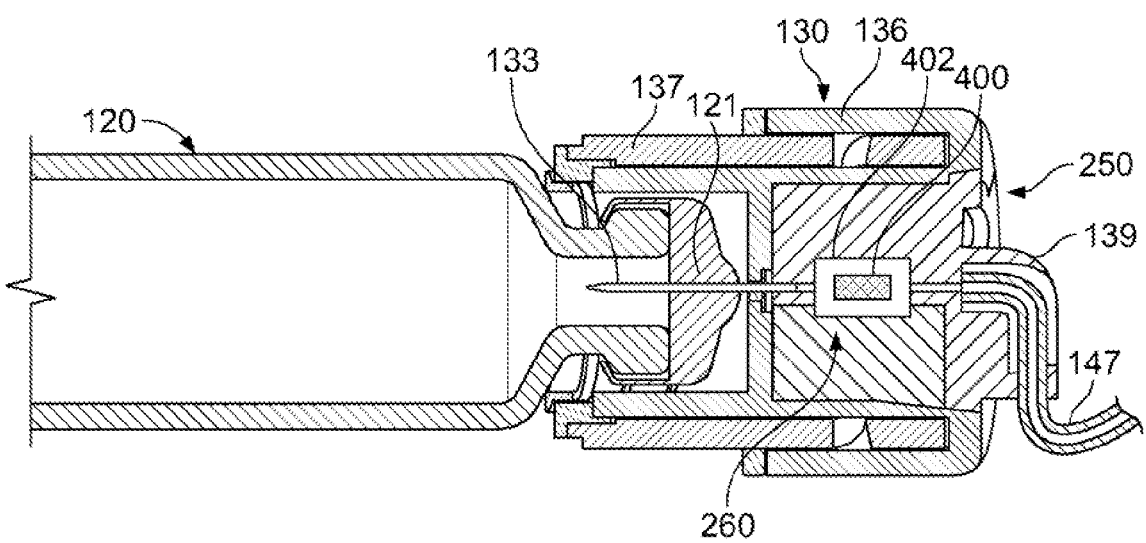
FIG. 20 is a cross-sectional view of the cap device of FIG. 19 including in occlusion sensor system.

Referring to FIG. 20, the cap device 130 can have a multi-piece construction that provides a flow path 260, which includes the chamber 402, from the medicine container 120 to the output port 139 (and to the infusion set tubing 147). In this embodiment, the flow sensor device 400 is located within the chamber 402. At least a portion of the flow sensor device 400 within the cap device 130 may be monitored by the sensor circuit 252 to determine if an occlusion exists (e.g., if a kink or clog exists in the infusion set tubing 147 of cannula 149).

The multi-piece construction of the cap device 130 can facilitate proper alignment of the cap device 130 and proper engagement with the medicine cartridge 120 during attachment of the cap device 130 to the pump housing 110. For example, the cap device 130 may include a first component 136 that is movably engaged with a second component 137. During attachment of the cap device 130 to the pump housing, the first component 136 can be rotated relative to the second component 137, which causes the second component 137 to advance longitudinally toward the medicine cartridge 120. In such circumstances, a needle penetrator 133 attached to the second component 137 can be advanced toward the septum 121 of the medicine cartridge 120 to pierce the septum and open a fluid flow path. The flow path for the medicine that is dispensed from the medicine cartridge 120 can pass through the needle penetrator 133, through a fluid channel 260, through the infusion set tubing 147, and to the user.

Figure 21:
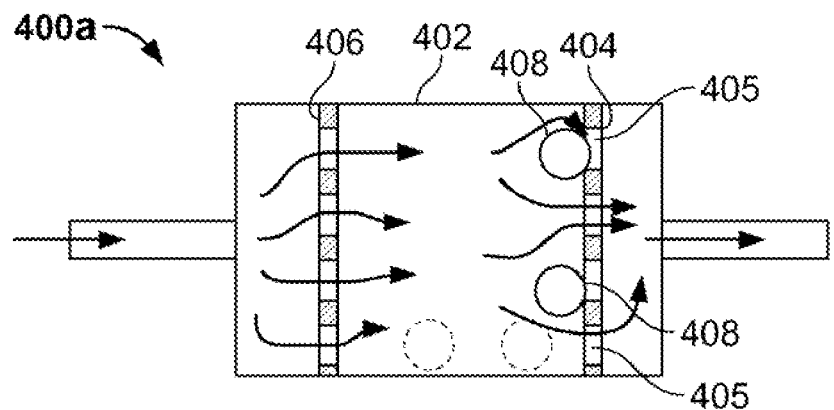
FIGS. 21-23 are schematic views of several exemplary embodiments of flow sensor devices of the occlusion sensor system.
Figure 22:
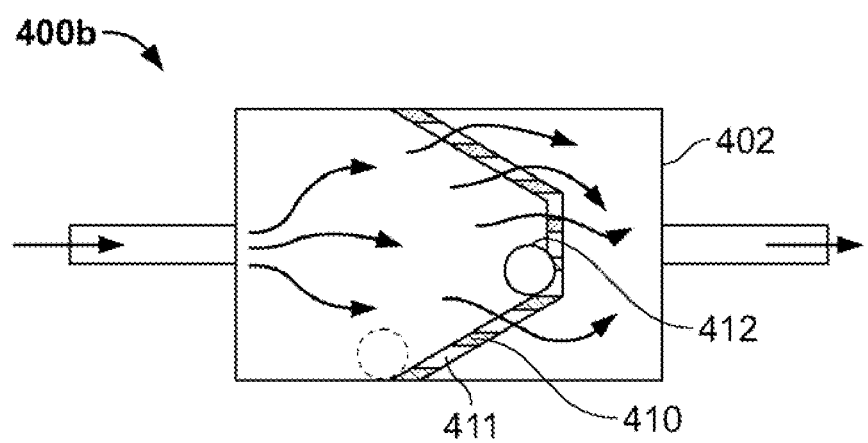
Figure 23:
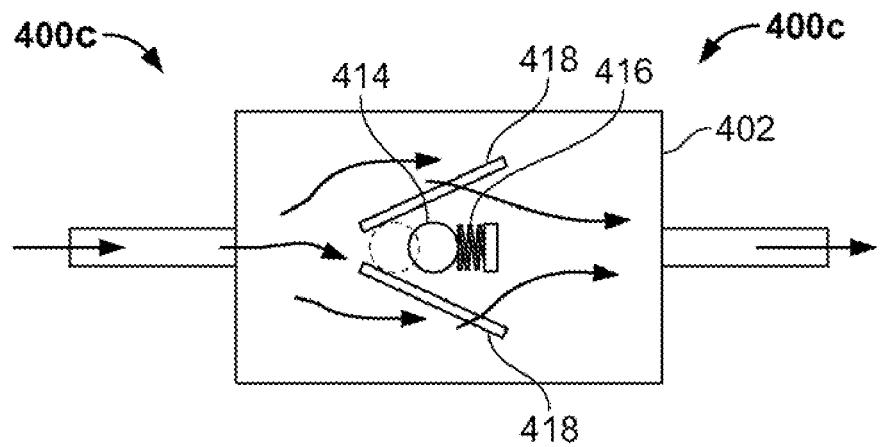

Referring to FIGS. 21-23, the flow sensor device 400 may have one of a number of different configurations capable of detecting flow characteristics within the chamber 400. In general, the flow sensor device 400 includes a sensor body or multiple sensor bodies, which are movable within the chamber 402. If fluid is flowing through the fluid channel 260 or at least a minimum fluid flow rate is present, the sensor body can move to a first (or flow) position by the fluid force acting thereon. If there is no fluid flow through the fluid channel 260 or the fluid flow rate is less than the minimum fluid flow rate, the sensor body may shift to a second (or rest) position.

The sensor circuit 252 detects whether one or more sensor bodies are in the first or second position. If the one or more sensor bodies are in the first position, the flow sensor device 400 communicates with the sensor circuit 252 to provide a sensor signal indicating that no occlusion exists. If the one or more sensor bodies are in the second position, the flow sensor device 400 communicates with the sensor circuit 252 to provide a sensor signal indicative of an occlusion in the flow path. In one embodiment, the sensor circuit 252 monitors the sensor device 400 to detect both the first and second positions of the one or more sensor bodies. In another embodiment, the sensor circuit 252 monitors the sensor device 400 to detect one of the first and second positions of the one or more sensor bodies. For example, in the case where the sensor circuit 252 monitors the first (flow) position, an occlusion is indicated when the sensor circuit 252 does not detect the presence of a sensor body in the first position. As discussed in further detail below, the sensor circuit 252 may monitor the flow sensor device 400 using optical, acoustical and/or electromagnetic instrumentation.

Referring to FIG. 21, one embodiment of a flow sensor device 400a includes first and second grates 404, 406 arranged in the chamber 402. The first grate 404 is located toward a downstream end of the chamber 402 and the second grate 406 is located toward an upstream end of the chamber 402. The first and second grates 404, 406 include openings 405 to allow fluid flow therethrough. In an alternative arrangement, the second grate 406 may be foregone. One or more sensor bodies 408, which are illustrated in the form of spheres, are located upstream of the first grate 404. Although spherical sensor bodies are illustrated in FIG. 21, the sensor bodies 408 may be configured to have another shape including, but not limited to, semi-spherical, cylindrical, cube, pyramid and the like. The sensor bodies 408 are larger than the openings 405 of the grates 404, 406, to prevent the sensor bodies 408 from passing therethrough.

When fluid flows through the chamber 402, the sensor bodies 408 are pushed towards and ultimately up against the first grate 404 in the first position (shown in solid lines). Preferably, the number of sensor bodies 408 is selected, such that fluid flow through the openings 405 of the first grate 404 is not significantly inhibited by the sensor bodies 408. In one embodiment, the sensor bodies 408 are sized such that the fluid flow rate through the chamber 402 must be greater than a minimum fluid flow rate in order to move the sensor bodies 408 to the first position (shown in solid lines). If there is no fluid flow through the chamber 402 or the fluid flow rate is less than the minimum fluid flow rate, there is insufficient fluid force to move the sensor bodies 408 to the first position and the sensor body 408 remain in the second position (shown in phantom lines). As explained in further detail below, the sensor circuit 252 monitors the position of the sensor bodies 408 using an optical instrument, an acoustic instrument, an electromagnetic instrument, or a combination thereof.

Referring now to FIG. 22, another embodiment of a flow sensor device 400b includes a single, conical shaped grate 410 having openings 411 to allow fluid flow therethrough. A sensor body 412, which is illustrated in the form of a sphere, is located upstream of the grate 410. Although a single sensor body 412 is illustrated, the flow sensor device 400b may include multiple sensor bodies 412. Again, the sensor body 412 may be configured to have another shape including, but not limited to, semi-spherical, cylindrical, cube, pyramid and the like. The sensor body 412 is larger than the openings of the grate 410, to prevent the sensor body 412 from passing therethrough.

When fluid is flowing through the chamber 402, the sensor body 412 is pushed towards and ultimately up against the vertex of the grate 410 to the first position (shown in solid line). In the case of multiple sensor bodies 412, the number of sensor bodies 412 can be selected, such that fluid flow through the grate 410 is not significantly inhibited. In one embodiment, the sensor body 412 is sized such that the fluid flow rate through the chamber 402 must be greater than a minimum fluid flow rate in order to move the sensor body 412 to the first position (shown in solid line). If there is no fluid flow through the chamber 402 or the fluid flow rate is less than the minimum fluid flow rate, there is insufficient fluid force to move the sensor body 412 to the first position and the sensor body 412 remains in the second position (shown in phantom line). As explained in further detail below, the sensor circuit 252 can monitor the position of the sensor body 412 to provide a signal indicative of whether an occlusion exists.

Referring now to FIG. 23, a third embodiment of a flow sensor device 400c includes a sensor body 414 that is mounted to a biasing member 416, which is supported within the chamber 402. Although a spherical sensor body 414 is illustrated, the sensor body 414 may be configured to have a different shape including, but not limited to, semi-spherical, cylindrical, cube, pyramid, cup-shaped and the like. When fluid is flowing through the chamber 402, the sensor body 414 is pushed against the biasing force of the biasing member 416, compressing the biasing member 416 and ultimately moving to the first position (shown in solid line). In one embodiment, the sensor body 414 and the biasing member 416 are sized such that the fluid flow rate through the chamber 402 must be greater than a minimum fluid flow rate in order to overcome the biasing force and move the sensor body 414 to the first position. If there is no fluid flow through the chamber 402 or the fluid flow rate is less than the minimum fluid flow rate, there is insufficient fluid force to overcome the biasing force of the biasing member 416 and move the sensor body 414. As a result, the sensor body 414 remains in the second position (shown in phantom line). In one embodiment, wall members 418 are located within the chamber 402 to help direct fluid flow therethrough. As explained in further detail below, the sensor circuit 252 can monitor the position of the sensor body 414 to provide a signal indicative of whether an occlusion exists.

Figure 24:
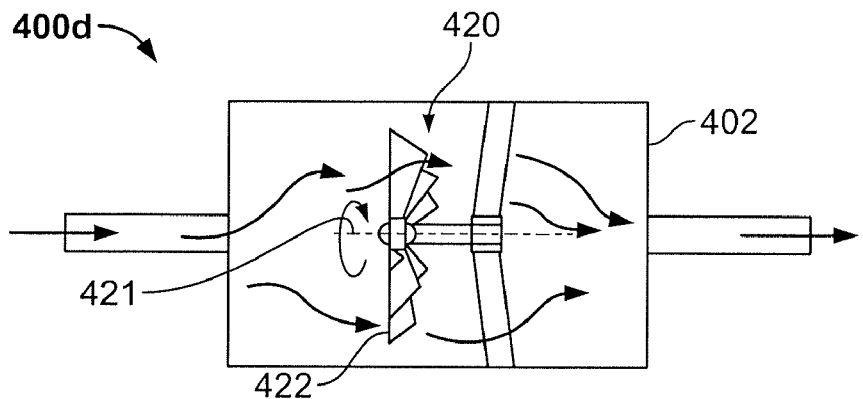
FIGS. 24-26 are schematic views of exemplary alternative embodiments of flow sensor devices of the occlusion sensor system.

Referring now to FIG. 24, a fourth embodiment of a flow sensor device 400d includes an impeller 420 that is supported for rotation within the chamber 402. The impeller 420 includes vanes 422, which resist fluid flow through the chamber 402. More specifically, fluid flowing through the chamber 402 acts on the vanes 422 to induce rotation of the impeller 420 about an axis of rotation 421. If there is no fluid flow or the flow rate is less than a minimum flow rate, the impeller 420 does not rotate or rotates with an angular velocity that is less than a threshold angular velocity. In such a case, the flow sensor device 400d and the sensor circuit 252 may communicate to produce a signal indicative of an occlusion. If the fluid flow rate through the chamber 402 is greater than a minimum fluid flow rate, the impeller 420 rotates with an angular velocity that is greater than the threshold angular velocity. In this case, the flow sensor device 400d and the sensor circuit 252 communicate to produce a signal indicating that an occlusion is not present. As explained in further detail below, the sensor circuit 252 can monitor the rotation of the impeller 420 using an optical instrument, an acoustical instrument, an electromagnetic instrument, or a combination thereof.

Figure 25A:
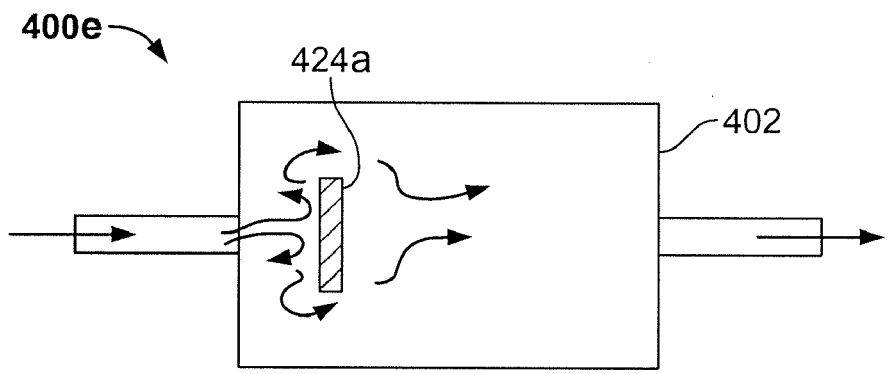

Referring now to FIG. 25A, a fifth embodiment of a flow sensor device 400e can include at least one wall member 424a that is disposed within the fluid path within the chamber 402. The wall member 424a functions to generate vortices or turbulence within the chamber 402, as fluid flows therethrough. More specifically, as fluid enters the chamber 402, the wall member 424a obstructs and redirects the fluid flow, creating a tortuous or turbulent fluid flow. In short, the wall member 424a functions as an abrupt obstruction in the fluid flow path. In this embodiment, the sensor circuit 252 acoustically monitors the fluid flow to determine whether an occlusion exists, as described in further detail below. Although the wall member 424a of FIG. 25A is illustrated as a rectangular wall member, the sensor device 400e can include a plurality of wall members 424a, which can be configured to have a different shape including, but are not limited to, rectangular, square, triangular, spherical, semi-spherical, concave, convex, cylindrical and the like.

Figure 25B:
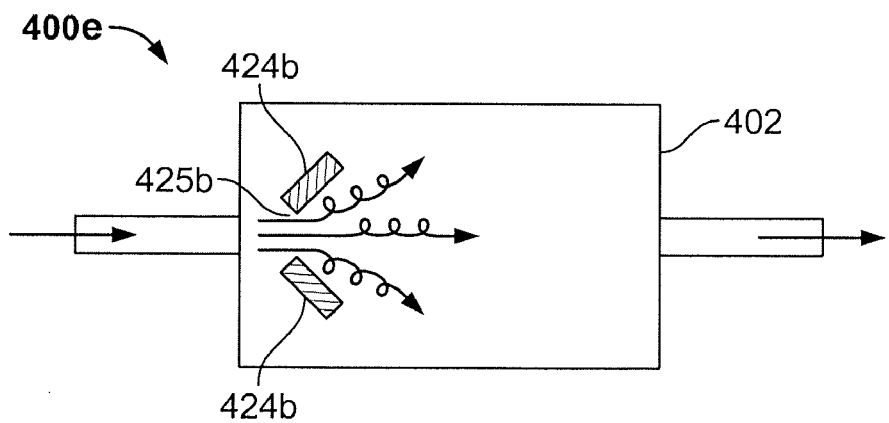

Referring now to FIG. 25B, an alternative embodiment of the flow sensor device 400e can include multiple wall members 424b that are disposed within the fluid path within the chamber 402. The wall members 424b are arranged to define an orifice or passage 425b. The wall members 424b and orifice 425b function to generate vortices or turbulence within the chamber 402, as fluid flows therethrough. More specifically, as fluid enters the chamber 402, the wall members 424b constrict the fluid flow at the orifice 425b. Consequently, the fluid accelerates through the orifice 425b, which functions as a nozzle, to create a tortuous or turbulent fluid flow. In this embodiment, the sensor circuit 252 can acoustically monitor the fluid flow to determine whether an occlusion exists, as described in further detail below.

Figure 25C:
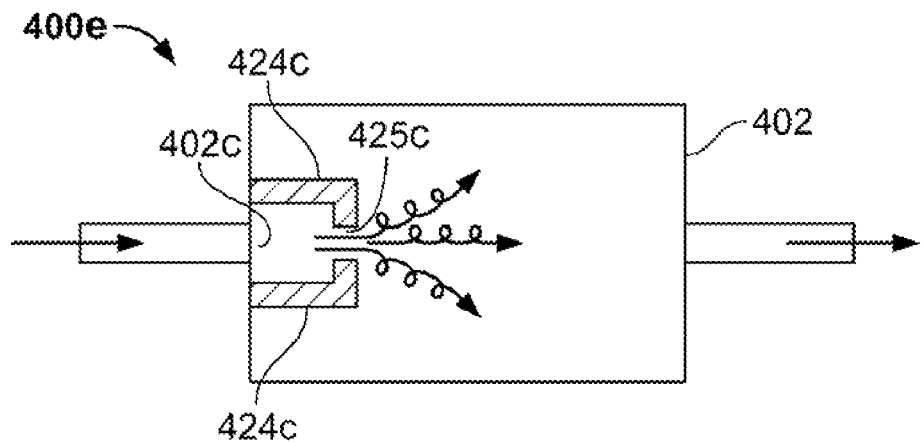

Referring now to FIG. 25C, still another alternative embodiment of the flow sensor device 400e can include multiple wall members 424c that are disposed within the fluid path within the chamber 402. The wall members 424c are arranged to define sub-chamber 402c and an orifice or passage 425c. The wall members 424c and orifice 425c function to generate vortices or turbulence within the chamber 402, as fluid flows therethrough. More specifically, as fluid enters the sub-chamber 402c, the wall members 424c constrict the fluid flow at the orifice 425c. Consequently, the fluid accelerates through the orifice 425c, which functions as a nozzle, to create a tortuous or turbulent fluid flow. In this embodiment, the sensor circuit 252 can acoustically monitor the fluid flow to determine whether an occlusion exists, as described in further detail below.

Figure 25D:
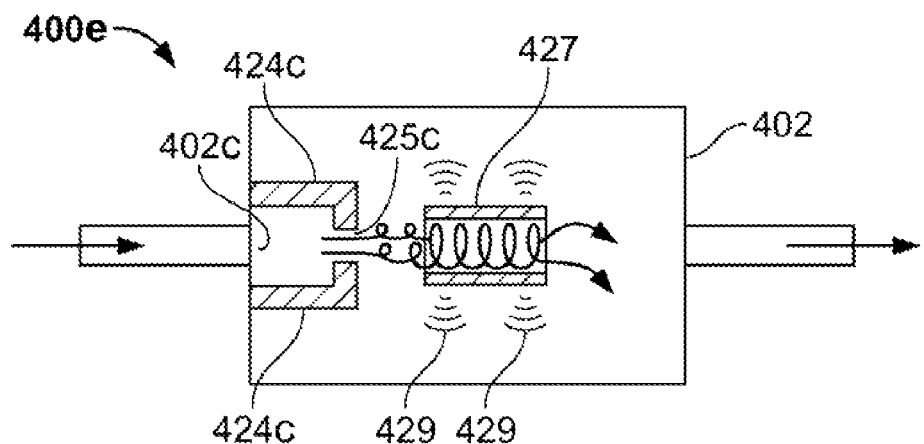

Referring now to FIG. 25D, yet another alternative embodiment of the flow sensor device 400e can include the multiple wall members 424c that are arranged to define sub-chamber 402c and an orifice or passage 425c, as described above referring to FIG. 25C. Again, the wall members 424c and orifice 425c function to generate vortices or turbulence within the chamber 402, as fluid flows therethrough. As fluid enters the sub-chamber 402c, the wall members 424c constrict the fluid flow at the orifice 425c. The flow sensor device 400e of FIG. 25D further includes a resonant structure or chamber 427. Consequently, the fluid accelerates through the orifice 425c, which functions as a nozzle, to create a tortuous or turbulent fluid flow. The fluid flow exiting the sub-chamber 402c flows into the resonant chamber 427. The fluid flow, which may be a turbulent fluid flow, reflects or echoes off of the walls of the resonant chamber 427. This echoing of the fluid flow within the resonant chamber 427 can induce additional acoustical waves 429 within the chamber 402. Again, the sensor circuit 252 can acoustically monitor the fluid flow to determine whether an occlusion exists, as described in further detail below.

Figure 26:
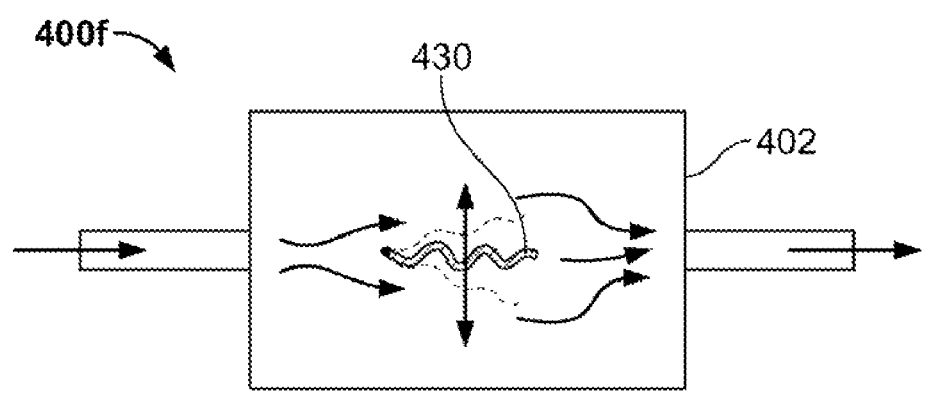

With reference to FIG. 26, a sixth embodiment of a flow sensor device 400f includes a resonant structure 430 that is supported along the fluid flow path within the chamber 402. Fluid flowing through the chamber 402 excites the resonant structure 430 and induces vibration of the resonant structure 430. Although the resonant structure 430 is illustrated as a plate having a wave-form cross-section, the resonant structure 430 can have other configurations. For example, the resonant structure 430 can include a ball or disc fixed to a flexure plate. The resonant structure 430 partially obstructs the fluid flow, such that the fluid flow induces vibration of the resonant structure 430 and causing the resonant structure 430 to oscillate, as indicated by the phantom lines. The sensor circuit 252 can monitor the resonant structure 430 using an optical instrument, an acoustical instrument, an electromagnetic instrument, or a combination thereof.

Figure 28:
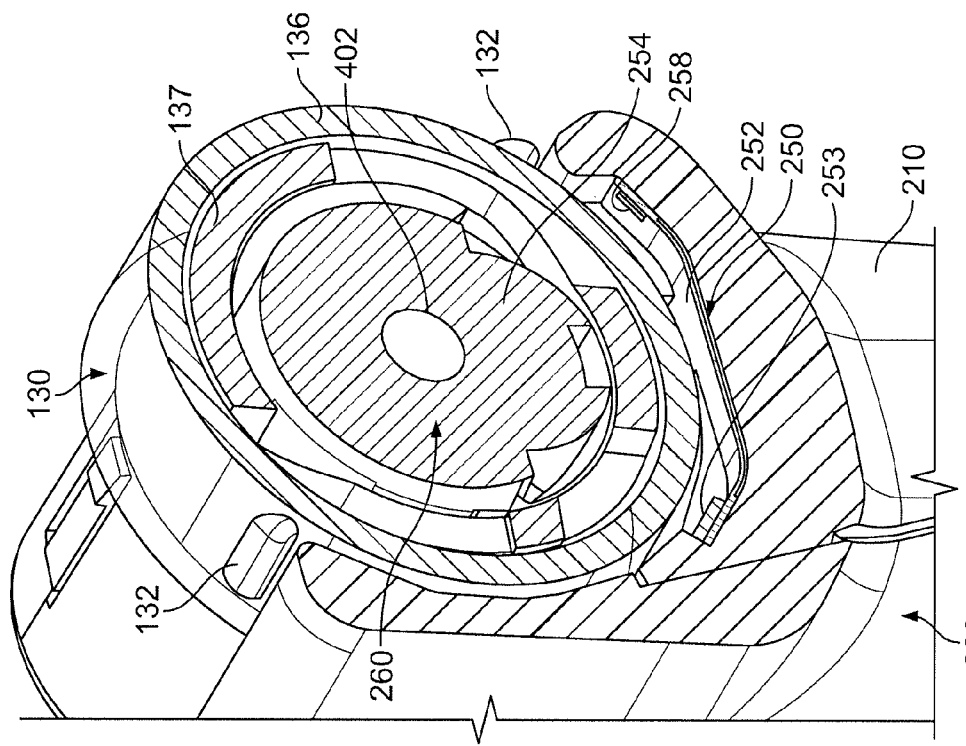
FIGS. 27 and 28 are cross-sectional views of the occlusion sensor system for use in an infusion pump system.
Figure 27:
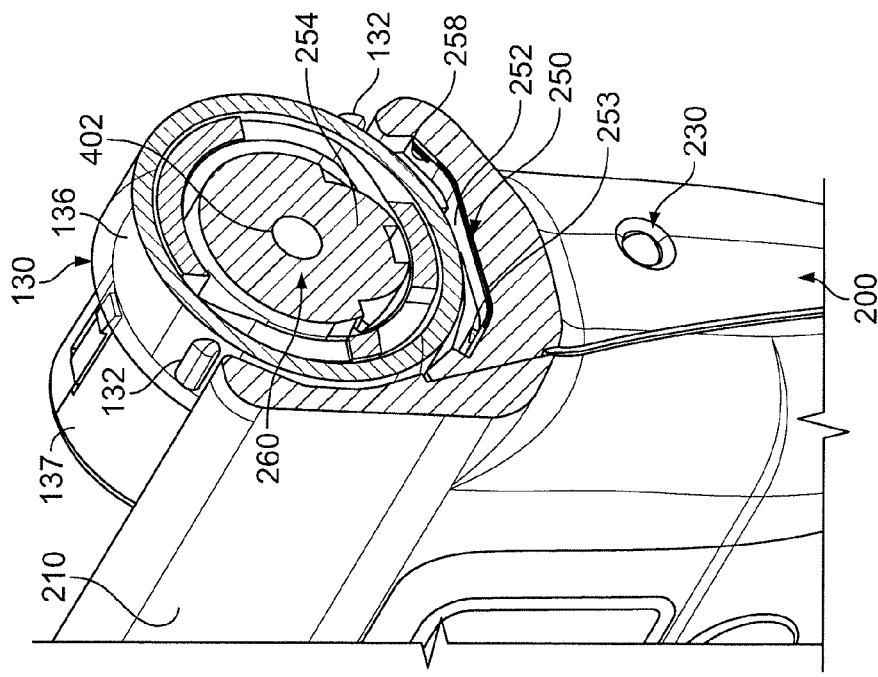
Figure 29:
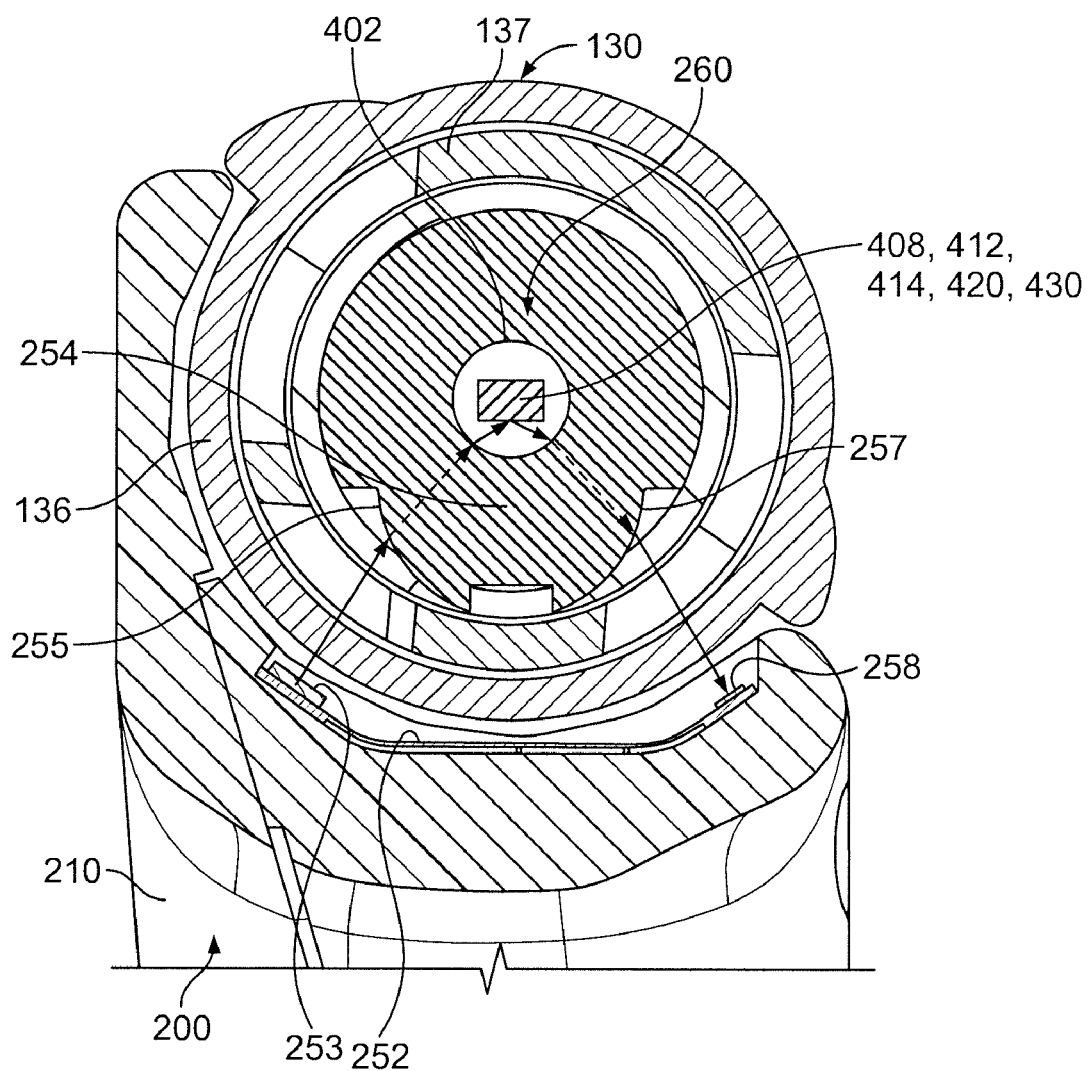
FIG. 29 is a cross-sectional view of the occlusion sensor system of FIGS. 27 and 28.

Referring to FIGS. 27-31, exemplary embodiments of the sensor circuit 252 include an optical instrument, an acoustical instrument, an electromagnetic instrument, or a combination thereof to monitor the flow sensor device 400. With particular reference to FIGS. 27-29, some embodiments of the sensor circuit 252 employ an optical detection process. The sensor circuit 252 can be arranged so that the fluid channel 260 and the chamber 402 in the cap device 130 is aligned with a light emitter 253 and a light sensor 258 when the pump device 100 is attached to the controller device 200. Thus, when the infusion pump system 10 is operating to dispense medicine, the light emitter 253 in the controller device 200 can direct light toward the chamber 402 in the cap device 130, and the light sensor 258 can receive light reflected from portions of the cap device 130. A cross-section through the cap device 130 and the controller device 200 (refer to FIGS. 27-28) illustrates one example of the alignment. It should be understood from the description herein that other alignment configurations can be implemented so that the light sensor 258 in the reusable controller device 200 is able to detect changes to fluid flow conditions in the pump device 100.

In this embodiment, the sensor circuit 252 is arranged to at least partially extend to the barrel channel 211 (FIGS. 4-5) of the controller device 200 so that the light emitter 253 and the light sensor 258 are positioned adjacent to the cap device 130. As previously described, the tabs 132 of the cap device 130 can be positioned in a manner that facilitates the particular orientation of the cap device 130 relative to the sensor circuit 252. The light from the light emitter 253 can pass through one or more portions of the cap device 130 during its travel toward the fluid channel 260 and chamber 402. Accordingly, some portions of the cap device 130 may comprise a generally transparent material to permit light transmission therethrough. In this embodiment, the first component 136 of the cap device 130 can include a generally transparent polymer material. Also, in some embodiments, some portions of the cap device 130 may include windows or openings to avoid interfering with the light from the light emitter 253. For example, the second component 137 may include openings at selected locations so that light from the light emitter 253 can pass by the second component 137 and to the internal light transmissive member 254.

Still referring to FIGS. 27-29, the internal light transmissive member 254 can be configured to receive light from the light emitter 253, transmit at least a portion of that light toward the chamber 402. In this embodiment, the internal light transmissive member 254 comprises a generally transparent polymer material that is capable of light transmission.

The occlusion sensor system 250 can be used to optically detect when an occlusion exists in the flow path from the pump device 100 to the user. For example, when an occlusion occurs in the infusion set tubing 147 (FIGS. 6-7), the delivery of medicine from the infusion pump system 10 to the user can be stopped or otherwise limited. If the user is unaware of the occlusion, the user may be deprived of the intended dosages of medicine from the infusion pump device for a period of time. Accordingly, the occlusion sensor system 250 can be used to detect when such occlusions occur in the flow path to the user, and the controller device 200 can thereafter alert the user of the occlusion when particular conditions are met. The user may then inspect the pump device 100 or the infusion set 146 to eliminate the occlusion.

As shown in FIG. 29, the light emitter 253 can emit light that is directed toward the internal light transmissive member 254. The light passes through the generally transparent first component 136 of the cap device 130 and then strikes a curved surface 255 of the internal light transmissive member 254. The light may be refracted at the interface with the internal light transmissive member 254. The curved surface 255 may operate as a focusing lens that directs the light toward the chamber 402. This light may be reflected within the chamber 402, as described in further detail below, and continues through the internal light transmissive member 254 toward a second curved surface 257. The second curved surface 257 may operate as a focusing lens that directs the light toward the light sensor 258. Upon receiving the light, the light sensor 258 generates electrical signals. These electrical signals from the light sensor 258 can be transmitted via the sensor circuit 252 to the control circuitry 240 (FIGS. 15 and 19) for processing to determine if an occlusion alarm should be provided to the user.

In one embodiment, the light is reflected by an object within the chamber 402, such as the sensor bodies 408, 412, 414 described in FIGS. 21-23. For example, the light can be directed or otherwise aimed towards the expected location of the sensor bodies when the sensor bodies are forced by the fluid flow to first position. If the sensor bodies are in the first position (i.e., fluid is flowing through the chamber 402), the light from the light emitter 253 is reflected toward the light sensor 258. If the sensor bodies are not in the first position (i.e., fluid is not flowing though the chamber 402), the light from the light emitter 253 is not reflected by the sensor bodies toward the light sensor 258. In this manner, the light sensor 258 can generate a signal indicative of the presence or absence of the sensor body in the first position. In an alternative embodiment, the light can be directed or otherwise aimed towards the expected location of the sensor bodies when the sensor bodies are not moved by the fluid flow to the first position (i.e., when the sensor bodies are in the second position). For example, if the sensor bodies are in the first position (i.e., fluid is flowing through the chamber 402), the light, which is directed toward the second position, is not reflected by the sensor bodies toward the light sensor 258. If the sensor bodies are not in the first position (i.e., fluid is not flowing though the chamber 402), the light is reflected by the sensor bodies toward the light sensor 258. Based on the presence or absence of light detected by the light sensor 258, the sensor circuit 252 can provide signals indicative of an occluded or a non-occluded state.

In another embodiment, the light is reflected by a moving object within the chamber 402, such as the impeller 420 of FIG. 24 or the resonant structure 430 of FIG. 26. For example, if the impeller 420 is rotating or the resonant structure 430 is oscillating (i.e., fluid is flowing though the chamber 402), light can be intermittently reflected to the light sensor 258 from the impeller 420 or the resonant structure 430. If the impeller 420 is not rotating or the resonant structure 430 is not oscillating (i.e., fluid is not flowing though the chamber 402), there is either zero light reflected to the light sensor 258 by the impeller 420 or the resonant structure 430, or light is continuously reflected to the light sensor 258 by the impeller 420 or resonant structure 430, depending upon the position of the impeller 420 or the resonant structure 430 within the chamber 402. The presence of an occlusion can be detected based on the light received by the light sensor 258. For example, if the light is intermittently reflected to the light sensor 258, the impeller 420 or the resonant structure 430 is deemed to be moving in response to fluid flowing through the chamber 402. Accordingly, the sensor circuit 252 can provide sensor signals that there is no occlusion present. If light is not received by the light sensor 258, or light is constantly received by the light sensor 258 (e.g., the impeller 420 is in a fixed rotational position, which constantly reflects light to the light sensor 258), the impeller 420 or the resonant structure 430 is stationary. In such circumstances, the sensor circuit 252 can provide sensor signals that indicate that there is an occlusion present.

In other embodiments, the occlusion detection can occur using other optical processes including a laser Doppler process or a particle imaging process. When using a laser Doppler process, the occlusion sensor system 250 generates a monochromatic laser beam that is directed toward a target (e.g., the chamber 402, the sensor bodies 408, 412, 414, the impeller 420 or the resonant structure 430). In such an embodiment, the light source 253 is a monochromatic laser light source. When the target is moving as a result of fluid flow through the chamber 402, some portion of the laser beam is reflected to the sensor 258. In accordance with the Doppler effect, the change in wavelength of the reflected radiation is a function of the target's relative movement. Thus, the movement of the target can be obtained by measuring the change in wavelength of the reflected laser light, which may be achieved by forming an interference fringe pattern (e.g., by superimposing the original and reflected signals). Accordingly, the presence or absence of a sensor body 408, 412, 414 in the first position and movement of the impeller 420 or the resonant structure can be detected by the sensor 258.

When using a particle imaging process, the light source 253 generates a planar laser light sheet. The light sheet is pulsed twice, for example, and portions of the light sheet are reflected to the light sensor 258 by objects (e.g., the sensor bodies 408, 412, 414). The light sensor 258 generates corresponding signals, from which the position of objects within the portion of the chamber 402 lying in the light sheet can be determined by the sensor circuit 252. Accordingly, a first location of an object can be determined based on a first light sheet pulse and a second location of the object can be determined based on a second light sheet pulse. The displacement of the object can be determined by the sensor circuit 252 based on the first and second locations. For example, displacement of the sensor bodies 408, 412, 414, rotation of the impeller 420 and oscillation of the resonant 430 structure can be determined. In one embodiment, the displacement can be measured by dividing the plane of the light sheet into small interrogation spots. The locations determined from two light sheet pulses are cross-correlated and the spatial displacement of the object (e.g., the sensor bodies 408, 412, 414, the impeller 420 and the resonant structure 430) within the chamber 402 is determined. The presence or absence of fluid flow within the chamber 402 can determined based on the spatial displacement.

Figure 30:
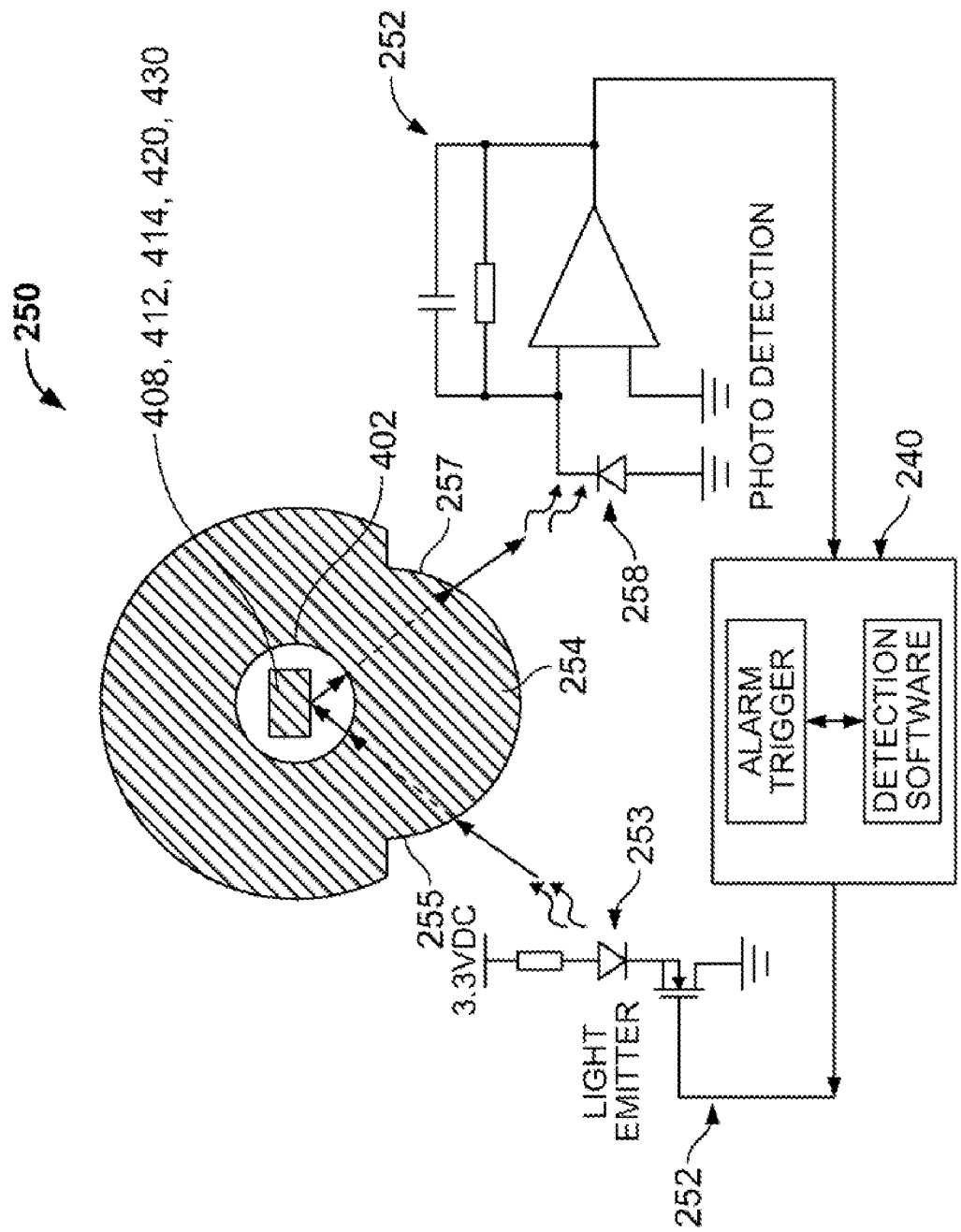
FIG. 30 is a schematic diagram of the occlusion sensor system of FIG. 29.

Referring to FIG. 30, the process of determining whether an occlusion exists can be implemented using the control circuitry 240 of the controller device 200. In particular, the control circuitry 240 can be used to activate the light emitter 253 and the light sensor 258 at selected times to monitor the fluid pressure in the flow path. For example, the control circuitry 240 can activate the light emitter 253 and the light sensor 258 one or more times before the drive system 300 (FIGS. 16-18) is activated to force medicine from the medicine cartridge 120, while the drive system 300 is activated, or after the drive system 300 is activated. The control circuitry 240 can receive detector signals from the light sensor 258 and thereafter process the data to determine if an alarm should be triggered to notify the user of an occlusion.

In this embodiment, the control circuitry 240 can activate the sensor circuit 252 one or more times while (or shortly after) the drive system 300 (FIGS. 16-18) is activated to force medicine from the medicine cartridge 120. When the sensor circuit 252 is activated, the light emitter 253 emits light toward the internal light transmissive member 254. The light may be again reflected in the chamber 402, as described above, and continue through the internal light transmissive member 254 toward the second curved surface 257. The second curved surface 257 may operate as a focusing lens that directs the light toward the light sensor 258. As previously described, in some embodiments, the light sensor 258 is capable of generating electrical signals upon receipt of the light. These electrical signals from the light sensor 258 can be transmitted via the sensor circuit 252 to the control circuitry 240. The control circuitry 240 receives the signals from the light sensor 258 and uses this data to determine if an occlusion alarm should be provided to the user.

The detection software module may include instructions to use the data signals from the light sensor 258 as input data for a comparative algorithm that determines if an occlusion exists. The comparative algorithm can, for example, compare the data values from the light sensor 258 to an initial value recorded when the pump device 100 was initially activated with no occlusions in the flow path. Alternatively, the comparative algorithm can, for example, average the data values from the light sensor 258 recorded over a predetermined period of time (e.g., 2 minutes, 5 minutes, 10 minutes, 30 minutes, or the like) or over a predetermined number of pump drive cycles (e.g., the last 3 drive cycles, the last 5 drive cycles, the last 10 drive cycles). Then, this average value can be compare to an initial value recorded when the pump device 100 was initially activated with no occlusions in the flow path. These comparative algorithms can be used to reduce the instances of "false alarms" that are provided to the user, and in some cases, can be used to reduce error created by noise in the sensor system. It should be understood from the description herein that, in other embodiments, the detection software module may employ other algorithms to process the data and thereby determine if an occlusion exists.

Figure 31:
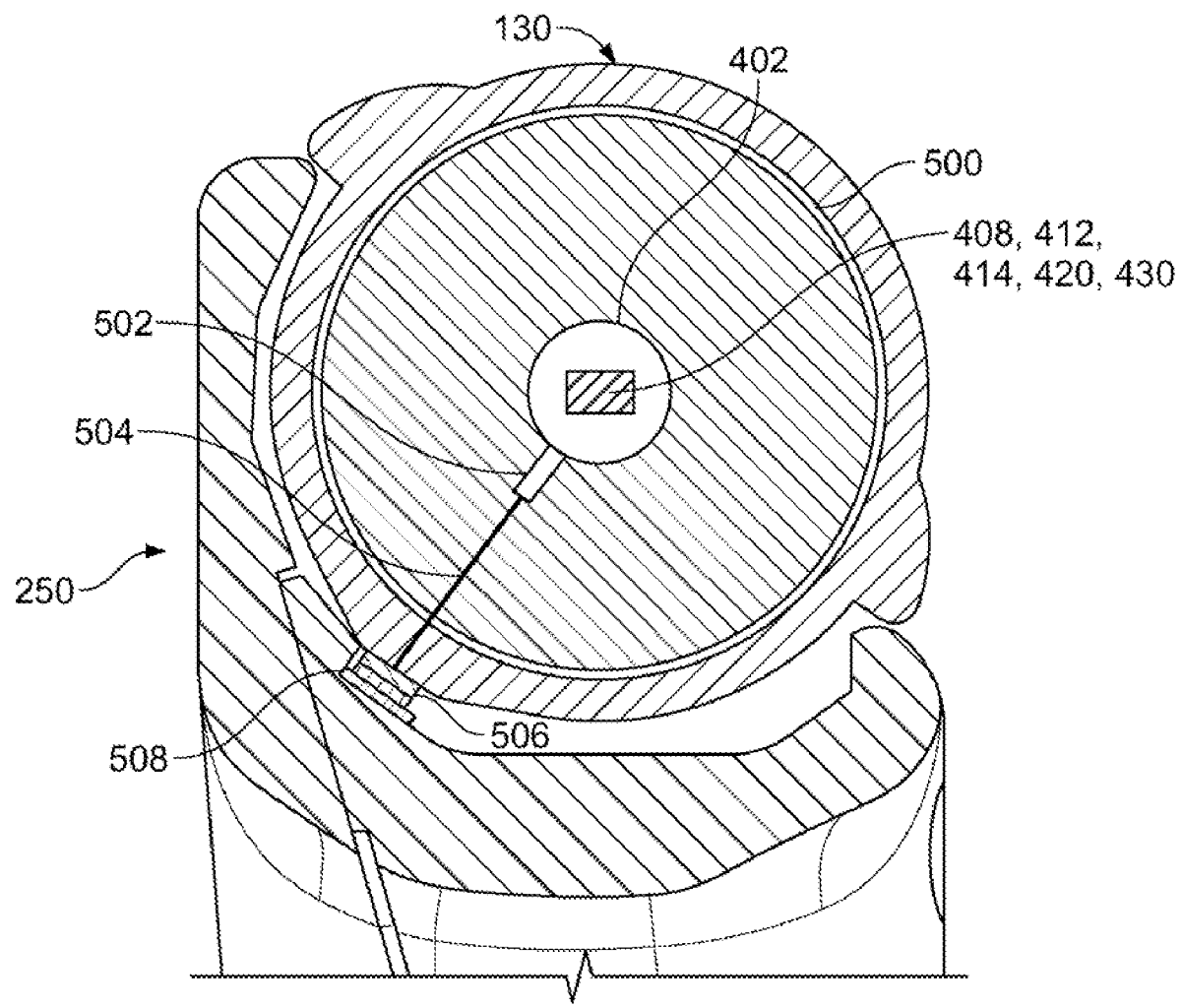
FIG. 31 is a cross-sectional view of an alternative embodiment of the occlusion sensor system.

Referring to FIG. 31, the occlusion sensor system 250 can be equipped with electromagnetic instrumentation or acoustic instrumentation to monitor the flow sensor device 400 in the chamber 402. In this embodiment, the cap device 130 includes a core 500 having the chamber 402 and fluid flow path 260 formed therein. The occlusion sensor system 250 includes a sensor 502, a lead 504 and first and second contacts 506, 508, respectively. The sensor 502 is disposed adjacent to the chamber 402 and can be separated from contact with the fluid flowing through the chamber 402. The sensor 502 can be electrically coupled to the first contact 506 through the lead 504. the second contact 508 can be electrically coupled to the control circuitry 240 (e.g., through the sensor circuitry or other flexible circuit). When the pump device 100 is assembled with the controller device 200, the cap device 130 is aligned such that the first contact 506 comes into secure electrical contact with the second contact 508. In this manner, an electrical connection between the sensor 502 and the control circuitry 240 is provided.

In one embodiment, the sensor 502 can be provided as an electromagnetic sensor that is responsive to changes in neighboring magnetic fields. For example, when a magnetic field is proximate to the sensor 502, components within the sensor 502 are excited, and the sensor 502 generates a signal in response. When the magnetic field is sufficiently remote from the sensor 502, the components are not excited or are less excited and there is no response signal generated. The magnetic field can be provided by a permanent magnet. For example, components of the flow sensor devices, described above with reference to FIGS. 21-24 and 26, can comprise a ferromagnetic material that generates a magnetic field, which may be detected by the sensor 502.

With reference to the flow sensor devices 400a, 400b and 400c of FIGS. 21-23, the sensor bodies 408, 412, 414, for example, may be made from a ferromagnetic material and can generate a permanent magnetic field in the chamber 402. The sensor 502 (FIG. 31) can be arranged such that it is in proximity to the permanent magnetic field when a sensor body 408, 412, 414 is in one of the first or second positions. For example, the sensor 502 can be arranged such that when the sensor body 408, 412, 414 is in the first position, the sensor 502 is in proximity to the magnetic field. In response to the magnetic field, the sensor 502 generates a signal that is sent to the control circuitry 240 via the lead 504 and the contacts 506, 508. The signal from the sensor 502 can be indicative of sensor body 408, 412, 414 being in the first position, which indicates that there is fluid flowing through the chamber 402. Alternatively, the sensor 502 can be arranged such that when the sensor body 408, 412, 414 is in the second position, the sensor 502 is in proximity to the magnetic field. In response to the magnetic field, the sensor 502 generates a signal that is sent to the control circuitry 240 via the lead 504 and the contacts 506, 508. The signal from the sensor 502 can be indicative of the sensor body 408, 412, 414 being in the second position, which indicates that there is no fluid flowing through the chamber 402.

With reference to the flow sensor device 400d of FIG. 24, the impeller 420 or portions of the impeller 420 (e.g., one or more vanes 422) can be made of a ferromagnetic material and can generate a magnetic field. The sensor 502 (FIG. 31) can be arranged such that the magnetic field from the impeller 420 intermittently acts upon the sensor 502 as the impeller 420 rotates. For example, in the case where all of the vanes 422 of the impeller 420 are made from a ferromagnetic material, the combined magnetic field will have an irregular pattern. As the impeller 420 is induced to rotate, the sensor 502 will be in intermittent proximity with stronger and weaker portions of the combined magnetic field and will generate a pulsed signal in response thereto. This pulsed signal can be communicated from the sensor 502 to the control circuitry 240 to indicate that the impeller 420 is rotating as a result of fluid flowing through the chamber 402. If the sensor 502 detects a generally constant signal from the magnetic field of the impeller 420, the control circuitry 240 can determine that the impeller 420 is not rotating as a result of no fluid flowing through the chamber 402.

In other embodiments, for example, in which a vane 422 of the impeller 420 provides a magnetic field, the sensor 502 can be in intermittent proximity to the magnetic field when the impeller 420 rotates. As such, a pulsed signal is generated by the sensor 502 and is communicated to the control circuitry 240, which indicates that the impeller 420 is rotating as the result of fluid flowing through the chamber 402. If the sensor 502 outputs a generally constant signal (i.e., the impeller 420 is generally stationary such that the sensor 502 is in constant proximity to the magnetic field) or outputs no signal (i.e., the impeller's rotational position is fixed such that the sensor 502 remains out of proximity to the magnetic field), the impeller 420 is not rotating, which indicates that there is no fluid flowing through the chamber 402, or the fluid flow is below a minimum flow rate. In another embodiment, ferromagnetic tabs can be located on the vanes 422 of the impeller 420, as opposed to the impeller 420 being made of a ferromagnetic material itself.

With reference to the flow sensor device 400f of FIG. 26, the resonant structure 430 can be made of a ferromagnetic material and can generate a magnetic field within the chamber 402. The sensor 502 (FIG. 31) is arranged such that it is in proximity to the magnetic field when the resonant structure 430 oscillates. Oscillation of the resonant structure 430 results in oscillation of the magnetic field that acts on the sensor 502. In response, the sensor 502 generates a pulsed signal that is communicated to the control circuitry 240, which indicates that the resonant structure 430 is oscillating due to fluid flowing through the chamber 402. If the sensor 502 outputs a constant signal, the control circuitry 240 can determine that the resonant structure 430 is not oscillating because no fluid is flowing through the chamber 402 or because the fluid flow rate is less than a minimum fluid flow rate.

Referring again to FIG. 31, some embodiments of the occlusion sensor system 250 includes a sensor 502 that operates as an acoustic sensor responsive to pressure waves generated within the chamber 402. For example, when one or more components of the flow sensor devices 400a-400f (refer to FIGS. 21-26) move within the chamber 402, pressure waves are generated and can be detected by the sensor 502.

With reference to the flow sensor devices 400a, 400b of FIGS. 21-22, respectively, the sensor bodies 408, 412 may generate pressure waves as they move within the chamber 402. For example, upon initiating fluid flow through the chamber 402, the sensor bodies 408, 412 will come into contact with the respective grates 404, 410. This initial contact between the sensor bodies 408, 412 and the grates 404, 410 may generate one or more pressure waves. With reference to the flow sensor device 400d of FIG. 24, the impeller 420 can generate pressure waves as it is induced to rotate within the chamber 402 due to fluid flow within the chamber 402. With reference to the flow sensor device 400e of FIG. 25, the one or more wall members 424 that are disposed within the fluid path within the chamber 402 can generate vortices or turbulent flow within the chamber 402. As a result, pressure waves are generated as the fluid flows through the chamber 402 and around the wall members 424. With reference to the flow sensor device 400f of FIG. 26, pressure waves can be generated as the resonant structure 430 is induced to oscillate by the fluid flowing through the chamber 402.

Referring again to FIG. 31, these pressure waves generated by the various flow sensor devices 400a-f described above can be detected by the sensor 502, which is configured to operate as an acoustical sensor in this embodiment. In response, the sensor 502 generates a pulsed signal that is communicated to the control circuitry 240. Such a pulsed signal communicated to the control circuitry 240 can be indicative of fluid flowing through the chamber 402. Conversely, if no pulsed signal is generated by the sensor 502 and communicated to the control circuitry 240, the control circuitry 240 can determine that there is no fluid flowing through the chamber 402.

Similar to previous embodiments described in connection with FIG. 30, the process of determining whether an occlusion exists can be implemented using the control circuitry 240 of the controller device 200. In particular, the control circuitry 240 can be used to monitor the pulsed signal from the sensor 502 at selected times. For example, the control circuitry 240 can monitor the pulsed signal from the sensor 502 one or more times before the drive system 300 (FIGS. 16-18) is activated to force medicine from the medicine cartridge 120, while the drive system 300 is activated, or after the drive system 300 is activated. The control circuitry 240 can receive the pulsed signals from the sensor 502 and thereafter process the data (e.g., using the detection software module) to determine if an alarm should be triggered to notify the user of an occlusion.

The detection software module may include instructions to use the data signals from the sensor 502 as input data for a comparative algorithm that determines if an occlusion exists. The comparative algorithm can, for example, compare the data values from the sensor 502 to an initial value recorded when the pump device 100 was initially activated with no occlusions in the flow path. Alternatively, the comparative algorithm can, for example, average the data values from the sensor 502 recorded over a predetermined period of time (e.g., 2 minutes, 5 minutes, 10 minutes, 30 minutes, or the like) or over a predetermined number of pump drive cycles (e.g., the last 3 drive cycles, the last 5 drive cycles, the last 10 drive cycles). Then, this average value can be compare to an initial value recorded when the pump device 100 was initially activated with no occlusions in the flow path. These comparative algorithms can be used to reduce the instances of "false alarms" that are provided to the user, and in some cases, can be used to reduce error created by noise in the sensor system. It should be understood from the description herein that, in other embodiments, the detection software module may employ other algorithms to process the data and thereby determine if an occlusion exists.

In these embodiments, in which the sensor circuit 252 uses an optical sensor, an acoustical sensor or an electromagnetic sensor, the control circuitry 240 can activate the alarm trigger module to alert the user if the detection software module indicates that an occlusion exists. The alarm trigger module can be used to activate the user interface 220 (FIGS. 1-2) to communicate one or more alarms. For example, the alarm trigger module of the control circuitry may be used to activate an audible alarm, a visual alarm (e.g., on the display device 222 (FIGS. 1-2)), or a combination thereof. In some embodiments, the alarm trigger module is configured to provide a set of escalating alarms. For example, the first stage of the alarm may include a low intensity audible alert followed by a textual alarm on the display device. If the user does not respond after a predetermined period of time (e.g., 10 seconds, 30 seconds, or the like), the alarm trigger module may then provide a high intensity audible alert (e.g., louder alert) in combination with a visual alarm having image effects on the display device (e.g., a blinking screen, alternating images, or the like). The alarm trigger module may include further stages of alarm if the user does not respond after a predetermined period of time. When the user is alerted to the occlusion in the flow path, the user can inspect the infusion set tubing 147 and the cannula 149 to determine if there is a repairable kink. If the occlusion is substantial, the user can suspend the operation of the infusion pump system 10 and replace the infusion set 146 with a new infusion set 146.

It should be understood from the description herein that the occlusion sensor system 250 is limited to embodiments that incorporate an optical sensor, an acoustical sensor, or an electromagnetic sensor. For example, in other embodiments, the sensor 502 can be a thermal mass-flow sensor. In such circumstances, the thermal mass-flow sensor 502 can also function as a heat source and can monitor the rate at which heat is absorbed by the fluid flow. The rate of heat absorbed by the fluid flow is directly proportional to its mass flow rate. More specifically, as molecules of the fluid are heated, they absorb heat and thereby cool the heat source. As the fluid flows, more molecules come into contact with the heat source, absorbing even more heat. The sensor 502 generates a signal corresponding to the amount of heat dissipated from the heat source. The sensor circuit 252 can determine the fluid flow rate based on the signal from the sensor 502.

It should be understood from the description herein that the occlusion sensor system 250 can have configurations other than the embodiments described in connection with FIGS. 19-31. For example, in some embodiments, the flow sensor device 400*a-f* (FIGS. 21-26) may be arranged in a portion of the pump device other than the cap 130. In general, the flow sensor device 400*a-f* can be arranged as part of the flow path. Further, the occlusion sensor system 250 can be arranged to provide a non-contact coupling between the fluid flow sensor device 400*a-f* and the sensor electronics. Such a non-contact coupling can be achieved optically, inductively, and/or magnetically. In this manner, the flow sensor device 400*a-f* can be sterilized separately and the sensor electronics can be reused, without concern for sterilization thereof.

A number of embodiments of the invention have been described. Nevertheless, it will be understood that various modifications may be made without departing from the spirit and scope of the invention. Accordingly, other embodiments are within the scope of the following claims.

What is claimed is:

1. A portable infusion pump system, comprising:
    a pump device including a pump housing that defines a space to receive a medicine, a separable cap device that mates with the pump housing to cover the space that receives the medicine, and a drive system arranged in the pump housing to dispense the medicine through a medicine flow path, wherein the cap device is matable with an infusion set having a length of flexible tubing;
    a controller device that is removably attachable to the pump device, the controller device including a controller housing and control circuitry that communicates with the drive system of the pump device; and
    an occlusion sensor system that communicates with the control circuitry to detect the presence of an occlusion in the medicine flow path, comprising:
        a flow-responsive component arranged within a flow chamber of the cap device of the pump device, the flow-responsive component moving in the flow chamber in response to medicine flow through the flow chamber and acting on the flow-responsive component; and
        a sensor circuit at least partially disposed within the controller device, the sensor circuit being arranged in the controller housing and adjacent to the cap device of the pump device so as to detect movement of the flow-responsive component to a first position while the controller device is removably attached to the pump device and the drive system in the pump housing urges medicine through the medicine flow path, the sensor circuit communicating a signal to the control circuitry in response to the movement of the flow-responsive component to the first position.

2. The pump system of claim 1, wherein the flow-responsive component includes at least one sensor body that is movable by the medicine flowing from the pump device.

3. The pump system of claim 2, wherein the sensor circuit monitors a magnetic field that is generated by the at least one sensor body.

4. The pump system of claim 2, wherein the sensor circuit monitors pressure waves generated by the at least one sensor body.

5. The pump system of claim 2, wherein the sensor circuit optically monitors a position of the at least one sensor body.

6. The pump system of claim 1, wherein the flow-responsive component includes an impeller that is rotatably supported within the flow chamber.

7. The pump system of claim 6, wherein the sensor circuit includes a sensor to detect movement of the impeller, the sensor comprising one of an optical sensor, an electromagnetic sensor and an acoustical sensor.

8. The pump system of claim 1, wherein the flow-responsive component includes at least one resonant structure that oscillates when the medicine flows through the flow chamber of the pump device.

9. The pump system of claim 8, wherein the sensor circuit includes a sensor to detect movement of the resonant structure, the sensor comprising one of an optical sensor, an electromagnetic sensor and an acoustic sensor.

10. A method of monitoring a wearable infusion pump system for occlusions, the method comprising:
    preparing a pump device for use with a controller device, the pump device including a pump housing that encloses at least an actuator portion of a drive system to dispense medicine from the pump device and a cap device that mates with the pump housing to cover a space that receives the medicine, the controller device including a controller housing and control circuitry to communicate control signals to the actuator portion of the drive system within the pump housing of the pump device;
    removably attaching the pump device with the controller device so that a first electrical connector of the pump device engages a second electrical connector of the controller device;
    aligning a flow-responsive component of an occlusion sensor system with a sensor circuit of the occlusion sensor system, the flow-responsive component being movable within a flow chamber of the cap device of the pump device and the sensor circuit being arranged in the controller housing and adjacent to the pump device so as to detect movement of the flow-responsive component to a first position within the pump device while the drive system in the pump housing urges medicine through the flow chamber of the pump device; and
    activating the occlusion sensor system to determine if the medicine is flowing from the pump device.

11. The method of claim 10, further comprising generating an alert of an occlusion in a medicine flow path when the occlusion sensor system indicates a lack of medicine flow from the pump device.

12. The method of claim 10, wherein the flow-responsive component comprises at least one sensor body within a medicine flow path of the pump device, wherein the at least one sensor body moves in response to the medicine flowing through the chamber.

13. The method of claim 12, further comprising monitoring a magnetic field that is generated by the at least one sensor body using the sensor circuit.

14. The method of claim 12, further comprising monitoring pressure waves generated by the at least one sensor body using the sensor circuit.

15. The method of claim 12, further comprising optically monitoring a position of the at least one sensor body using the sensor circuit.

16. The method of claim 10, further comprising biasing the flow-responsive component against a flow direction of the medicine using a biasing member that exerts a biasing force on the flow-responsive component.

17. The method of claim 10, wherein the flow-responsive component includes an impeller that is rotatably supported within the flow chamber.

18. The method of claim 17, wherein the sensor circuit includes one of an optical sensor, an electromagnetic sensor and an acoustical sensor that monitors rotation of the impeller.

19. The method of claim 14, wherein the flow-responsive component includes at least one resonant structure that oscillates when medicine flows through the chamber.

20. The method of claim 19, wherein the sensor circuit includes one of an optical sensor, an electromagnetic sensor and an acoustical sensor that monitors movement of the resonant structure.

21. A portable and wearable infusion pump assembly, comprising:
 a disposable and non-reusable pump device including: a drive system to dispense a medicine from the pump device, a pump housing to enclose at least a portion of the drive system, a separable cap device that mates with the pump housing to cover a space that receives the medicine, and a first electrical connector that is externally accessible along the pump housing;
 a reusable controller device removably attached to the pump device, the controller device including: a user interface having a display device and at least one button, control circuitry to communicate with the drive system of the pump device, a controller housing to enclose at least a portion of the control circuitry, and a second electrical connector is engaged with the first connector to provide electrical communication between the control circuitry and the drive system; and
 an occlusion sensor system that communicates with the control circuitry to detect the presence of an occlusion in a medicine flow path, the occlusion sensor system comprising:
  a flow-responsive component arranged within a flow chamber of the separable cap device of the pump device, the flow-responsive component moving in the flow chamber in response to medicine flow through the flow chamber and acting on the flow-responsive component; and
  a sensor circuit at least partially disposed within the controller device, the sensor circuit being arranged to detect movement of the flow-responsive component to a first position, the sensor circuit communicating a signal to the control circuitry in response to the movement of the flow-responsive component to the first position.

22. The infusion pump assembly of claim 21, wherein the flow-responsive component includes at least one sensor body positioned in the separable cap device of the pump device, and the sensor circuit includes one of an optical sensor, an electromagnetic sensor and an acoustical sensor that is mounted to the controller housing and that monitors movement of the at least one sensor body.

23. The infusion pump assembly of claim 21, wherein the flow-responsive component includes an impeller that is rotatably supported within the flow chamber, and the sensor circuit includes one of an optical sensor, an electromagnetic sensor and an acoustical sensor that monitors rotation of the impeller.

24. The infusion pump assembly of claim 21, wherein the flow-responsive component includes at least one resonant structure that oscillates when fluid flows through the flow chamber, and the sensor circuit includes one of an optical sensor, an electromagnetic sensor and an acoustical sensor that monitors movement of the at least one resonant structure.

25. A wearable infusion pump system, comprising:
 a disposable and non-reusable pump device including a drive system to dispense medicine from the pump device and a cap device to cover a space that receives the medicine, the controller device including a first electrical connector that is externally accessible;
 a reusable controller device removably attachable to the disposable and non-reusable pump device, the controller device including a second electrical connector that is engageable with the first connector to provide electrical communication between control circuitry of the controller device and the drive system of the pump device; and
 an occlusion sensor system that communicates with the control circuitry to detect the presence of an occlusion in a medicine flow path, the occlusion sensor system comprising:
  an obstruction member arranged in a stationary position within a flow chamber of the cap device of the pump device, the obstruction member remaining stationary in a medicine flow path to generate disturbances within the medicine flow path in response to medicine flow through the flow chamber; and
  a sensor circuit at least partially disposed within the controller device, the sensor circuit being arranged to detect the disturbances in the medicine flow path, the sensor circuit communicating a signal to the control circuitry in response to the disturbances.

26. The system of claim 25, wherein the obstruction member comprises at least one wall member is disposed within the flow chamber that remains generally stationary in the flow chamber, wherein the obstruction member and the flow chamber are positioned within the cap device of the pump device.

27. The system of claim 26, wherein the at least one wall member generates the disturbances including vortices or turbulence within the flow chamber in response to the drive system in the pump housing urges medicine through the flow chamber of the pump device.

28. The system of claim 27, wherein the sensor circuit acoustically monitors the disturbances in the medicine flow path.

29. The system of claim 25, wherein the obstruction member comprises a resonant structure that is supported along the medicine flow path within the flow chamber.

30. The system of claim 29, wherein medicine flow through the flow chamber induces vibration of the resonant structure, and the sensor circuit monitors the vibration of the resonant structure.

* * * * *